US007935797B2

(12) United States Patent
Allaway et al.

(10) Patent No.: US 7,935,797 B2
(45) Date of Patent: May 3, 2011

(54) CCR5 CHEMOKINE RECEPTOR-SPECIFIC MONOCLONAL ANTIBODIES CAPABLE OF INHIBITING HIV-1 CELL FUSION

(75) Inventors: Graham P. Allaway, Mohegan Lake, NY (US); Virginia M. Litwin, Fayetteville, NY (US); Paul J. Maddon, Elmsford, NY (US); William C. Olson, Ossining, NY (US)

(73) Assignee: Progenics Pharmaceuticals Inc., Tarrytown, NY (US)

( * ) Notice: Subject to any disclaimer, the term of this patent is extended or adjusted under 35 U.S.C. 154(b) by 658 days.

(21) Appl. No.: 11/894,568

(22) Filed: Aug. 20, 2007

(65) Prior Publication Data
US 2008/0138897 A1     Jun. 12, 2008

Related U.S. Application Data

(63) Continuation of application No. 09/460,216, filed on Dec. 13, 1999, which is a continuation of application No. PCT/US98/12331, filed on Jun. 12, 1998, which is a continuation-in-part of application No. 08/876,078, filed on Jun. 13, 1997, now Pat. No. 6,107,019, which is a continuation-in-part of application No. 08/831,823, filed on Apr. 2, 1997, now Pat. No. 6,344,545.

(60) Provisional application No. 60/019,715, filed on Jun. 14, 1996, provisional application No. 60/014,532, filed on Apr. 2, 1996.

(51) Int. Cl.
C12P 21/08     (2006.01)
(52) U.S. Cl. .................................. 530/388.75
(58) Field of Classification Search ............ None
See application file for complete search history.

(56) References Cited

U.S. PATENT DOCUMENTS

| | | | |
|---|---|---|---|
| 5,225,539 A | 7/1993 | Winter | |
| 5,817,767 A | 10/1998 | Allaway | |
| 5,939,320 A | 8/1999 | Littman | |
| 6,025,154 A | 2/2000 | Li et al. | |
| 6,100,087 A | 8/2000 | Rossi et al. | |
| 6,107,019 A | 8/2000 | Allaway et al. | |
| 6,258,527 B1 | 7/2001 | Littman | |
| 6,258,782 B1 | 7/2001 | Barney et al. | |
| 6,261,763 B1 | 7/2001 | Allaway et al. | |
| 6,265,184 B1 | 7/2001 | Gray | |
| 6,268,477 B1 | 7/2001 | Gray | |
| 6,344,545 B1 | 2/2002 | Allaway et al. | |
| 6,448,375 B1 | 9/2002 | Samson | |
| 6,528,625 B1 * | 3/2003 | Wu et al. .................. | 530/388.22 |
| 6,548,636 B2 | 4/2003 | Dragic | |
| 6,692,745 B2 | 2/2004 | Olson | |
| 6,692,938 B2 | 2/2004 | Samson | |
| 6,759,519 B2 | 7/2004 | Li et al. | |
| 6,797,811 B1 | 9/2004 | Gray | |
| 6,800,447 B2 | 10/2004 | Samson | |
| 6,908,734 B2 | 6/2005 | Dragic et al. | |
| 6,930,174 B2 | 8/2005 | Samson et al. | |
| 7,129,055 B2 | 10/2006 | Littman et al. | |
| 7,160,546 B2 | 1/2007 | Li et al. | |
| 7,175,988 B2 | 2/2007 | Roschke et al. | |
| 7,345,153 B2 | 3/2008 | Litwin et al. | |
| 7,501,123 B2 | 3/2009 | Roschke et al. | |
| 2002/0045161 A1 | 4/2002 | Allaway et al. | |
| 2002/0048786 A1 | 4/2002 | Rosen et al. | |
| 2002/0061834 A1 | 5/2002 | Rosen et al. | |
| 2002/0068813 A1 | 6/2002 | Dragic et al. | |
| 2002/0177603 A1 | 11/2002 | Johnson et al. | |
| 2003/0003440 A1 | 1/2003 | Lopalco | |
| 2003/0092632 A1 | 5/2003 | Dragic et al. | |
| 2003/0139571 A1 | 7/2003 | Dragic et al. | |
| 2003/0166024 A1 | 9/2003 | Rosen et al. | |
| 2003/0166870 A1 | 9/2003 | Wu et al. | |
| 2003/0195348 A1 | 10/2003 | Combadiere et al. | |
| 2004/0062767 A1 | 4/2004 | Olson et al. | |
| 2004/0110127 A1 | 6/2004 | Samson et al. | |
| 2004/0161739 A1 | 8/2004 | Samson et al. | |
| 2005/0131042 A1 | 6/2005 | Flentge | |
| 2005/0154193 A1 | 7/2005 | Roschke et al. | |
| 2006/0154857 A1 | 7/2006 | Redfield et al. | |
| 2007/0026441 A1 | 2/2007 | Olson et al. | |
| 2007/0231327 A1 | 10/2007 | Olson et al. | |
| 2007/0274986 A1 | 11/2007 | Olson et al. | |

FOREIGN PATENT DOCUMENTS
CA     2216990     12/1997
(Continued)

OTHER PUBLICATIONS
U.S. Appl. No. 10/081,128, filed Feb. 22, 2002, W.C. Olson et al.
U.S. Appl. No. 09/212,793, filed Feb. 16, 1998, W.C. Olson et al.
U.S. Appl. No. 08/663,616, filed Jun. 14, 1996, G.P. Allaway et al.
U.S. Appl. No. 08/673,682, filed Jun. 25, 1996, G.P. Allaway et al.
U.S. Appl. No. 08/874,570, filed Jun. 13, 1997, G.P. Allaway et al.
U.S. Appl. No. 08/874,618, filed Jun. 13, 1997, G.P. Allaway et al.

(Continued)

Primary Examiner — Jeffrey S. Parkin
(74) Attorney, Agent, or Firm — John P. White; Cooper & Dunham LLP

(57) ABSTRACT

This invention provides methods for inhibiting fusion of HIV-1 to CD4$^+$ cells which comprise contacting CD4$^+$ cells with a non-chemokine agent capable of binding to a chemokine receptor in an amount and under conditions such that fusion of HIV-1 to the CD4$^+$ cells is inhibited. This invention also provides methods for inhibiting HIV-1 infection of CD4$^+$ cells which comprise contacting CD4$^+$ cells with a non-chemokine agent capable of binding to a chemokine receptor in an amount and under conditions such that fusion of HIV-1 to the CD4$^+$ cells is inhibited, thereby inhibiting the HIV-1 infection. This invention provides non-chemokine agents capable of binding to the chemokine receptor and inhibiting fusion of HIV-1 to CD4$^+$ cells. This invention also provides pharmaceutical compositions comprising an amount of the non-chemokine agent capable of binding to the chemokine receptor and inhibiting fusion of HIV-1 to CD4$^+$ cells effective to prevent fusion of HIV-1 to CD4$^+$ cells and a pharmaceutically acceptable carrier.

1 Claim, 10 Drawing Sheets

FOREIGN PATENT DOCUMENTS

| | | |
|---|---|---|
| EP | 96870021.1 | 3/1996 |
| EP | 96870102 | 8/1996 |
| EP | 0815137 | 12/1996 |
| EP | 1145721 A2 | 10/2001 |
| EP | 1146055 A2 | 10/2001 |
| EP | 1146122 A2 | 10/2001 |
| EP | 1148126 A2 | 10/2001 |
| EP | 1148127 A2 | 10/2001 |
| EP | 1149582 A2 | 10/2001 |
| EP | 1199360 A2 | 4/2002 |
| EP | 0883687 B1 | 10/2004 |
| EP | 1482042 A1 | 12/2004 |
| WO | WO 94/19017 | 9/1994 |
| WO | WO 97/22698 | 6/1997 |
| WO | WO 97/28258 | 8/1997 |
| WO | WO 97/32019 | 9/1997 |
| WO | WO 97/37005 | 10/1997 |
| WO | WO 97/44055 | 11/1997 |
| WO | WO 97/44462 | 11/1997 |
| WO | WO 97/47318 | 12/1997 |
| WO | WO 98/18826 | 5/1998 |
| WO | WO 01/55439 | 8/2001 |
| WO | WO 01/58915 | 8/2001 |
| WO | WO 01/58916 | 8/2001 |
| WO | WO 01/64710 | 9/2001 |
| WO | WO 02/22077 | 3/2002 |
| WO | WO 02/064612 | 8/2002 |
| WO | WO 02/068608 | 9/2002 |
| WO | WO 02/083172 | 10/2002 |
| WO | WO 03/072766 | 9/2003 |
| WO | WO 2007/014114 | 2/2007 |

OTHER PUBLICATIONS

U.S. Appl. No. 09/118,415, filed Jul. 17, 1998, V.M. Litwin et al.
U.S. Appl. No. 60/358,886, filed Feb. 22, 2002, W.C. Olson et al.
U.S. Appl. No. 60/017,157, filed Feb. 20, 1996, D. Littman et al.
U.S. Appl. No. 60/266,738, filed Feb. 6, 2001, W.C. Olson et al.
U.S. Appl. No. 60/282,380, filed Apr. 6, 2001, W.C. Olson et al.
U.S. Appl. No. 60/019,715, filed Jun. 14, 1996, W.C. Olson et al.
U.S. Appl. No. 60/019,941, filed Jun. 14, 1996, G.P. Allaway et al.
U.S. Appl. No. 60/112,532, filed Dec. 16, 1998, W.C. Olson et al.
U.S. Appl. No. 60/185,667, filed Feb. 29, 2000, T. Dragic.
U.S. Appl. No. 60/205,839, filed May 19, 2000, T. Dragic.
U.S. Appl. No. 60/267,231, filed Feb. 7, 2001, T. Dragic.
U.S. Appl. No. 60/272,203, filed Feb. 28, 2001, T. Dragic.
U.S. Appl. No. 60/018,508, filed May 28, 1996, C. Combadiere et al.
Feb. 15, 1996 Advisory Action in connection with U.S. Appl. No. 08/169,311.
Sep. 13, 1995 Final Office Action in connection with U.S. Appl. No. 08/169,311.
Nov. 23, 1994 Office Action in connection with U.S. Appl. No. 08/169,311.
Aug. 18, 1994 Office Action in connection with U.S. Appl. No. 08/169,311.
Jul. 16, 1998 Notice of Acceptance in connection with Australian Application No. 14387/95.
Nov. 27, 1996 Examiner's First Report in connection with Australian Application No. 14387/95.
Jul. 5, 2000 Notice of Acceptance in connection with Australian Application No. 62690/96.
Nov. 10, 1998 Examiner's First Report in connection with Australian Application No. 62690/96.
Sep. 14, 2006 Official Action in connection with Canadian Application No. 2,224,003.
Sep. 11, 2006 Communication Pursuant to Article 96(2) EPC in connection with European Application No. 96 921 473.3.
Mar. 8, 2006 Summons to Oral Proceedings Pursuant to Rule 71(1) EPC in connection with European Application No. 96 921 473.3.
Feb. 24, 2005 Provision of a the Minutes in accordance with Rule 76(4) EPC in connection with European Application No. 96 921 473.3.
Feb. 24, 2005 Decision to Refuse a European Patent Application in connection with European Application No. 96 921 473.3.
Aug. 30, 2004 Summons to Oral Proceedings Pursuant to Rule 71(1) EPC in connection with European Application No. 96 921 473.3.
Dec. 19, 2002 Communication Pursuant to Article 96(2) EPC in connection with European Application No. 96 921 473.3.
Jul. 6, 2001 Communication Pursuant to Article 96(2) EPC in connection with European Application No. 96 921 473.3.
Dec. 20, 1999 Notice of Allowance and Allowability in connection with U.S. Appl. No. 08/973,601.
Aug. 3, 1999 Advisory Action in connection with U.S. Appl. No. 08/973,601.
Mar. 25, 1999 Office Action in connection with U.S. Appl. No. 08/973,601.
Jun. 24, 1998 Office Action in connection with U.S. Appl. No. 08/973,601.
Jan. 11, 2005 Notice of Allowance and Allowability in connection with U.S. Appl. No. 09/412,284.
Dec. 2, 2003 Final Office Action in connection with U.S. Appl. No. 09/412,284.
Feb. 3, 2003 Office Action in connection with U.S. Appl. No. 09/412,284.
Apr. 8, 2002 Advisory Action in connection with U.S. Appl. No. 09/412,284.
Sep. 11, 2001 Final Office Action in connection with U.S. Appl. No. 09/412,284.
Dec. 19, 2000 Office Action in connection with U.S. Appl. No. 09/412,284.
Apr. 18, 2007 Office Action in connection with U.S. Appl. No. 11/258,963.
Dec. 26, 2006 Office Action in connection with U.S. Appl. No. 11/258,963.
Feb. 8, 2007 Office Action in connection with U.S. Appl. No. 09/904,356.
May 2, 2006 Final Office Action in connection with U.S. Appl. No. 09/904,356.
Oct. 12, 2005 Office Action in connection with U.S. Appl. No. 09/904,356.
Jul. 29, 2005 Advisory Action in connection with U.S. Appl. No. 09/904,356.
Nov. 17, 2004 Final Office Action in connection with U.S. Appl. No. 09/904,356.
Jul. 1, 2003 Office Action in connection with U.S. Appl. No. 09/904,356.
Sep. 29, 2003 Advisory Action in connection with U.S. Appl. No. 09/118,415.
Jan. 28, 2003 Final Office Action in connection with U.S. Appl. No. 09/118,415.
Apr. 9, 2002 Office Action in connection with U.S. Appl. No. 09/118,415.
Aug. 14, 2001 Advisory Action in connection with U.S. Appl. No. 09/118,415.
Nov. 24, 2000 Final Office Action in connection with U.S. Appl. No. 09/118,415.
Feb. 11, 2000 Office Action in connection with U.S. Appl. No. 09/118,415.
Aug. 3, 2006 Notice of Allowance and Allowability in connection with U.S. Appl. No. 09/891,062.
Jul. 17, 2006 Notice of Allowability in connection with U.S. Appl. No. 09/891,062.
May 18, 2006 Notice of Allowance and Allowability in connection with U.S. Appl. No. 09/891,062.
Aug. 8, 2005 Office Action in connection with U.S. Appl. No. 09/891,062.
Mar. 21, 2005 Office Action in connection with U.S. Appl. No. 09/891,062.
May 28, 2004 Advisory Action in connection with U.S. Appl. No. 09/891,062.
Sep. 24, 2003 Final Office Action in connection with U.S. Appl. No. 09/891,062.
Dec. 18, 2002 Office Action in connection with U.S. Appl. No. 09/891,062.
Apr. 30, 2007 Notice of Allowance and Allowability in connection with U.S. Appl. No. 11/544,346.

Mar. 3, 1997 Office Action in connection with U.S. Appl. No. 08/627,684.
Jun. 23, 1997 Office Action in connection with U.S. Appl. No. 08/663,616.
Mar. 13, 1997 Office Action in connection with U.S. Appl. No. 08/673,682.
Nov. 28, 2000 Notice of Acceptance in connection with Australian Application No. 26074/97.
Jul. 13, 1999 Examiner's First Report in connection with Australian Application No. 26074/97.
Oct. 23, 2006 Official Action in connection with Canadian Application No. 2,250,829.
May 27, 2005 Official Action in connection with Canadian Application No. 2,250,829.
May 4, 2007 Summons to Attend Oral Proceedings Pursuant to Rule 71(1) EPC in connection with European Application No. 97917856.3.
Jan. 27, 2006 Communication Pursuant to Article 96(2) EPC in connection with European Application No. 97917856.3.
Oct. 21, 2005 Communication Pursuant to Article 115(2) EPC in connection with European Application No. 97917856.3.
Apr. 1, 2005 Communication Pursuant to Article 96(2) EPC in connection with European Application No. 97917856.3.
Aug. 5, 2004 Communication Pursuant to Article 96(2) EPC in connection with European Application No. 97917856.3.
Jan. 27, 2004 Communication Pursuant to Article 96(2) EPC in connection with European Application No. 97917856.3.
May 9, 2003 Communication Pursuant to Article 96(2) EPC in connection with European Application No. 97917856.3.
Mar. 6, 2002 Search Report Communication in connection with European Application No. 97917856.3.
Feb. 27, 2007 Notification of Reasons for Rejection in connection with Japanese Application No. 535610/97 (English translation).
May 19, 2006 Examiner's First Report in connection with Australian Application No. 2004233505.
Jul. 26, 2004 Notice of Acceptance in connection with Australian Application No. 35106/01.
Jul. 5, 2004 Examiner's Second Report in connection with Australian Application No. 35106/01.
Nov. 1, 2002 Examiner's First Report in connection with Australian Application No. 35106/01.
Dec. 4, 2001 Notice of Allowance and Allowability in connection with U.S. Appl. No. 08/831,823.
Jan. 16, 2001 Notice of Allowance and Allowability in connection with U.S. Appl. No. 08/831,823.
Sep. 26, 2000 Advisory Action in connection with U.S. Appl. No. 08/831,823.
Apr. 11, 2000 Final Office Action in connection with U.S. Appl. No. 08/831,823.
Jul. 21, 1999 Final Office Action in connection with U.S. Appl. No. 08/831,823.
Dec. 21, 1998 Office Action in connection with U.S. Appl. No. 08/831,823.
Aug. 17, 1998 Office Action in connection with U.S. Appl. No. 08/831,823.
Jun. 15, 2006 Final Office Action in connection with U.S. Appl. No. 09/888,938.
Sep. 7, 2005 Office Action in connection with U.S. Appl. No. 09/888,938.
Aug. 4, 2004 Office Action in connection with U.S. Appl. No. 09/888,938.
May 5, 2004 Office Action in connection with U.S. Appl. No. 09/888,938.
Jun. 22, 1999 Notice of Allowance and Allowability in connection with U.S. Appl. No. 08/876,078.
Dec. 21, 1998 Final Office Action in connection with U.S. Appl. No. 08/876,078.
Mar. 23, 1998 Office Action in connection with U.S. Appl. No. 08/876,078.
Jun. 16, 2006 Communication Pursuant to Article 96(2) EPC in connection with European Application No. 98 931 261.6.
Jun. 17, 2005 Communication Pursuant to Article 96(2) EPC in connection with European Application No. 98 931 261.6.
Oct. 17, 2006 Final Office Action in connection with U.S. Appl. No. 09/460,216.
Feb. 3, 2006 Office Action in connection with U.S. Appl. No. 09/460,216.
July 29, 2005 Advisory Action in connection with U.S. Appl. No. 09/460,216.
Feb. 9, 2005 Final Office Action in connection with U.S. Appl. No. 09/460,216.
Sep. 26, 2003 Advisory Action in connection with U.S. Appl. No. 09/460,216.
Feb. 27, 2003 Final Office Action in connection with U.S. Appl. No. 09/460,216.
Oct. 2, 2001 Office Action in connection with U.S. Appl. No. 09/460,216.
Sep. 9, 2002 Notice of Acceptance in connection with Australian Application No. 81426/98.
Feb. 27, 2002 Examiner's Second Report in connection with Australian Application No. 81426/98.
Feb. 21, 2001 Examiner's First Report in connection with Australian Application No. 81426/98.
Feb. 4, 1997 Office Action in connection with U.S. Appl. No. 08/665,090.
Aug. 29, 2000 Notice of Allowance and Allowability in connection with U.S. Appl. No. 08/874,618.
Nov. 19, 1999 Office Action in connection with U.S. Appl. No. 08/874,618.
May 24, 1999 Final Office Action in connection with U.S. Appl. No. 08/874,618.
Sep. 2, 1998 Office Action in connection with U.S. Appl. No. 08/874,618.
Dec. 13, 2005 Final Office Action in connection with U.S. Appl. No. 09/724,105.
Mar. 23, 2005 Office Action in connection with U.S. Appl. No. 09/724,105.
Sep. 23, 2004 Office Action in connection with U.S. Appl. No. 09/724,105.
May 19, 2004 Office Action in connection with U.S. Appl. No. 09/724,105.
Dec. 19, 2006 Office Action in connection with U.S. Appl. No. 11/400,497.
Aug. 8, 2006 Office Action in connection with U.S. Appl. No. 11/400,497.
May 29, 2001 Notice of Acceptance in connection with Australian Application No. 34026/97.
Sep. 28, 1999 Examiner's First Report in connection with Australian Application No. 34026/97.
Nov. 10, 2006 Official Action in connection with Canadian Application No. 2,257,991.
May 23, 2005 Communications Pursuant to Article 96(2) EPC in connection with European Application No. 97 930 120.7.
Nov. 17, 2004 Communication of partial European search report under Rule 45 EPC in connection with European Application No. 97 930 120.7.
Sep. 9, 2004 Communication of partial European search report under Rule 46(1) EPC in connection with European Application No. 97 930 120.7.
Oct. 17, 2006 Notification of Reasons for Rejection in connection with Japanese Application No. 501895/98 (English translation).
Apr. 5, 2004 Notice of Acceptance in connection with Australian Application No. 21996/00.
Feb. 5, 2003 Examiner's First Report in connection with Australian Application No. 21996/00.
Mar. 29, 2006 Examiner's First Report in connection with Australian Application No. 20004205164.
Mar. 29, 2006 Examiner's First Report in connection with Australian Application No. 20004205165.
Mar. 1, 2006 Communication under Rule 51(4) EPC in connection with European Application No. 99 966 466.7.
Jan. 10, 2005 Communication Pursuant to Article 96(2) EPC in connection with European Application No. 99 966 466.7.
Oct. 14, 2004 Communication Pursuant to Article 96(1) and Rule 51(1) EPC in connection with European Application No. 99 966 466.7.

Jan. 18, 2007 Office communication in connection with Mexican Application No. 1006097.
Oct. 13, 2005 Office communication in connection with Mexican Application No. 1006097.
Feb. 6, 2007 Notice of Allowability in connection with U.S. Appl. No. 09/464,902.
Jan. 8, 2007 Notice of Allowance and Allowability in connection with U.S. Appl. No. 09/464,902.
Apr. 19, 2006 Office Action in connection with U.S. Appl. No. 09/464,902.
Oct. 21, 2005 Office Action in connection with U.S. Appl. No. 09/464,902.
Jun. 15, 2005 Advisory Action in connection with U.S. Appl. No. 09/464,902.
Jan. 13, 2005 Final Office Action in connection with U.S. Appl. No. 09/464,902.
Apr. 2, 2004 Office Action in connection with U.S. Appl. No. 09/464,902.
Oct. 21, 2003 Office Action in connection with U.S. Appl. No. 09/464,902.
Sep. 25, 2001 Office Action in connection with U.S. Appl. No. 09/464,902.
Aug. 7, 2006 Office Action in connection with U.S. Appl. No. 09/594,983.
Mar. 24, 2006 Notice of Allowance and Allowability in connection with U.S. Appl. No. 09/594,983.
Jul. 11, 2005 Final Office Action in connection with U.S. Appl. No. 09/594,983.
Aug. 25, 2004 Office Action in connection with U.S. Appl. No. 09/594,983.
Sep. 23, 2003 Notice of Allowability in connection with U.S. Appl. No. 09/594,983.
Dec. 3, 2002 Final Office Action in connection with U.S. Appl. No. 09/594,983.
Mar. 13, 2002 Office Action in connection with U.S. Appl. No. 09/594,983.
Sep. 28, 2001 Office Action in connection with U.S. Appl. No. 09/594,983.
Dec. 19, 2006 Notice of Allowance and Allowability in connection with U.S. Appl. No. 10/763,545.
Jul. 26, 2006 Office Action in connection with U.S. Appl. No. 10/763,545.
Jun. 13, 2006 Office Action in connection with U.S. Appl. No. 10/763,545.
Feb. 16, 2006 Office Action in connection with U.S. Appl. No. 10/763,545.
May 16, 2006 Notice of Allowance and Allowability in connection with U.S. Appl. No. 10/371,483.
Oct. 24, 2006 Office Action in connection with U.S. Appl. No. 10/371,483.
Jan. 29, 2007 Examiner's First Report in connection Australian Application No. 2003217674.
Feb. 22, 2007 Communication Pursuant to Article 96(2) EPC in connection with European Application No. 03 713 632.2.
Apr. 21, 2006 Supplementary European search report under Article 157(2)(a) in connection with European Application No. 03 713 632.2.
Oct. 12, 2004 Communication Pursuant to Rules 109 and 110 EPC in connection with European Application with New Zealand Application No. 534947.
Mar. 14, 2006 Examination Report in connection with New Zealand Application No. 534947.
Feb. 21, 2003 Official Action in connection with Russian Federation Application No. 2004128252/13(030609) (English Translation).
Sep. 29, 2006 Grant of Patent in connection with Singaporean Application No. 200404610-8.
Aug. 7, 2002 Office Action in connection with U.S. Appl. No. 09/663,219.
Jan. 5, 2006 Notice of Allowability and Allowability in connection with U.S. Appl. No. 09/912,824.
Jan. 26, 2005 Final Office Action in connection with U.S. Appl. No. 09/912,824.
Apr. 20, 2004 Office Action in connection with U.S. Appl. No. 09/912,824.
Jul. 2, 2003 Office Action in connection with U.S. Appl. No. 09/912,824.
Jul. 3, 2006 Notice of Acceptance in connection with Australian Application No. 2001290925.
Jun. 28, 2005 Examiner's First Report in connection with Australian Application No. 2001290925.
May 24, 2006 Supplementary European search report under Article 157(2)(a) EPC in connection with European Application No. 01970984.9.
Feb. 28, 2005 Formalities Examination in connection with European Application No. 01970984.9.
May 2, 2003 Communication Pursuant to Rules 109 and 110 EPC in connection with European Application No. 01970984.9.
Oct. 25, 2005 Notice of Allowance and Allowability in connection with U.S. Appl. No. 09/828,615.
Sep. 13, 2005 Office Action in connection with U.S. Appl. No. 09/828,615.
Mar. 2, 2005 Office Action in connection with U.S. Appl. No. 09/828,615.
Sep. 17, 2004 Final Office Action in connection with U.S. Appl. No. 09/828,615.
Feb. 23, 2004 Office Action in connection with U.S. Appl. No. 09/828,615.
Sep. 9, 2003 Advisory Action in connection with U.S. Appl. No. 09/828,615.
Feb. 21, 2003 Final Office Action in connection with U.S. Appl. No. 09/828,615.
Jun. 25, 2002 Office Action in connection with U.S. Appl. No. 09/828,615.
Jun. 9, 2005 Notice of Allowance and Allowability in connection with U.S. Appl. No. 10/116,797.
Apr. 25, 2005 Final Office Action in connection with U.S. Appl. No. 10/116,797.
Oct. 6, 2004 Office Action in connection with U.S. Appl. No. 10/116,797.
Feb. 9, 2004 Office Action in connection with U.S. Appl. No. 10/116,797.
Sep. 7, 2005 Office Action in connection with U.S. Appl. No. 09/888,938.
Genbank Sequence Report, Accession Entry X91492 for *H. sapiens* Chem13, submitted Sep. 14, 1995.
Janeway and Travers (1994). Immunobiology, Current Biology Ltd., San Francisco. pp. 10:27-10:42.
Stryer (1988). Biochemistry, 3rd edition. pp. 984-988.
Dec. 17, 2003 Third Party Observations in connection with European Application No. 97904948.3.
Feb. 27, 2004 Third Party Observations in connection with European Application No. 97904948.3.
Abaza, M.S.I. and Astassi, M.Z. (1992). Effects of Amino Acid Substitutions Outside an Antigenic Site on Protein Binding to Monoclonal Antibodies of Predetermined Specificity Obtained by Peptide Immunization: Demonstration With Region 94-100 (Antigenic Site 3) of Myoglobin. J. Prot. Chem., 11(5):433-443.
Alkhatib, et al. (1996). Abstract at 3rd Conference on Retroviruses.
Alkhatib, G., et al. (1996). CC CKR5: A RANTES, MIP-1a, MIP-1β Receptor as a Fusion Cofactor for Macrophage-Tropic HIV-1. Science, 272:1955-1958.
Alkhatib, G., et al. (1997). HIV Co-Receptor Activity of CCR5 and Its Inhibition by Chemokines: Independence From G Protein Signaling and Importance of Co-Receptor Down Modulation. Virology, 234:340-348.
Allaway, G.P., et al. (1993). Synergistic Inhibition of HIV-1 Envelope-Mediated Cell Fusion by CD4-Based Molecules in Combination With Antibodies to gp120 or gp41. AIDS Res. Hum. Retroviruses, 9:581-587.
Allaway, G.P., (1995). Expression and Characterization of CD4-IgG2, a Novel Heterotetramer That Neutralizes Primary HIV Type 1 Isolates. AIDS Res. Hum. Retrovirus, 11:533-539.

Amara, A., et al. (1997). HIV Coreceptor Downregulation as Antiviral Principle: SDF-La-Dependent Internalization of the Chemokine Receptor CXCR4 Contributes to Inhibition of HIV Replication. J. Exp. Med., 186:139-146.

Arenzana-Selsdedos, F., et al. (1996). HIV Blocked by Chemokine Antagonist. Nature, 383:400.

Arthos, J., et al. (1989). Identification of the Residues in Human CD4 Critical for the Binding of HIV. Cell, 57:469-481.

Ashorn, P.A., et al. (1990). Human Immunodeficiency Virus Envelope Glycoprotein/CD4 Mediated Fusion of Nonprimate Cells With Human Cells. J. Virol., 64:2149-2156.

Attanasio, et al. (1991). Anti-Idiotypic Antibody Response to Monoclonal Anti-CD4 Preparations in Nonhuman Primate Species. J. Immunol., 146:507-514.

Baba, et al. (1998). Mechanism of Inhibitory Effect of Dectran Sulfate and Heparin on Replication of Human Immunodeficiency Virus in Vitro. Proc. Natl. Acad. Sci., 85:6132-6135.

Back, D.J. (1999). Pharmacological Issues Relating to Viral Resistance. Infection, 27(Suppl.2):S42-S44.

Balzarini, et al. (1995). Suppression of the Breakthrough of HIV-1 in Cell Culture by Thiocarboxanilide Derivatives When Used Individually or in Combination With Other HIV-1-Specific Inhibitors. Proc. Natl. Acad. Sci., 92:5470-5474.

Baulerle and Huttner (1987). Tyrosine Sulfation is a Trans-Golgi-Specific Protein Modification.. Cell. Biol., 105:2655-2663.

Berger, et al. (1996). Abstract No. 002, 8 at Keystone Symposium.

Berger E.A. (1997). HIV Entry and Tropism: The Chemokine Receptor Connection. AIDS, 11 (Suppl.A):S3-S16.

Berger, et al. (1999). Chemokine Receptors As HIV-1 Coreceptors: Roles in Viral Entry, Tropism and Disease. Ann. Rev. Immunol., 17:657-700.

Bieniasz, P.D., et al. (1997). HIV-1 Induced Cell Fusion is Mediated by Multiple Regions Within Both the Viral Envelope and the CCR5 Co-Receptor. EMBO, 16:2599-2609.

Blanpain, C., et al. (1999). Multiple Charged and Aromatic Residues in CCR5 Amino-Terminal Domain are Involved in High Affinity Binding of Both Chemokines and HIV-1 Env Protein. J. Biol. Chem., 274:34719-34727.

Bleul, C.C., et al. (1991). The Lymphocyte Chemoattractant SDF-1 is a Ligand for LESTR/Fusion and Blocks HIV-1 Entry. Nature, 382:829-832.

Brelot, A., et al. (1997). Role of the First and Third Extracellular Domains of CXCR4 in Human Immunodeficiency Virus Coreceptor Activity. J. Virol., 71:4744-4751.

Brenner, T.J., et al. (1996). Relation Between HIV-1 Syncytium Inhibition Antibodies and Clinical Outcome in Children. Lancet, 337:1001-1005.

Broder, et al. (1993). The Block to HIV-1 Envelope Glycoprotein-Mediated Membrane Fusion in Animal Cells Expressing Human CD4 can be Overcome by a Human Cell Component(S). Virol., 193:483-491.

Broder, et al. (1996). HIV and the 7-Transmembrane Domain Receptors. Pathobiology, 64(4):171-179.

Burkly, L., et al. (1995). Synergistic Inhibition of Human Immunodeficiency Virus Type 1 Envelope Glycoprotein-Mediated Cell Fusion and Infection by an Antibody to CD4 Domain 2 in Combination With Anti-Gp-120 Antibodies. J. Virol., 69:4267-4273.

Burton, D.R., et al. (1994). Efficient Neutralization of Primary Isolates of HIV-1 by a Recombinant Human Monoclonal Antibody. Science, 266.1024-1027.

Busso, et al. (1991). HIV-Induced Syncytium Formation Requires the Formation of Conjugates Between Virus-Infected and Uninfected T-Calls in Vitro. AIDS, 5:1425-1432.

Cammack, N. (1999). Human Immunodeficiency Virus Type 1 Entry and Chemokine Receptors: A New Therapeutic Target Antiviral Chemistry and Chemotherapy, 10:53-62.

Capon, D.J., et al. (1989). Designing CD4 Immunoadhesions for AIDS Therapy. Nature, 337:525-531.

Chan, D.C., et al. (1998). Evidence That a Prominent Cavity in the Coiled Coil of HIV Type 1 Gp41 is an Attractive Drug Target. Proc. Natl. Acad. Sci., 95:15613-15617.

Chan, D.C., et al. (1998). HIV Entry and Its Inhibition. Cell, 93:681-684.

Charo, et al. (1994). Molecular Cloning and Functional Expression of Two Monocyte Chemoattractant Protein 1 Receptors Reveals Alternative Splicing of the Carboxyl-Terminal Tails. Proc. Natl. Acad. Sci., 91:2752-2756.

Chen, et al. (1997). Genetically Divergent Strains of Simian Immunodeficiency Virus Use CCR5 As a Coreceptor for Entry. J. of Virol., 71(4):2705-2714.

Choe, H., et al. (1996). The Beta-Chemokine Receptors CCR3 and CCR5 Facilitate Infection by Primary HIV-1 Isolates. Cell, 85:1135-1148.

Clapham, P.R., et al. (1991). Specific Cell Surface Requirements for the Infection of CD4-Positive Cells by Human Immunodeficiency Virus Types 1 and 2 by Simian Immunodeficiency Virus. Virol., 181:703-715.

Co, et al. (1991). Humanized Antibodies for Antiviral Therapy. Proc. Natl. Acad. Sci., 88:2869-2873.

Cocchi, F. (1995). Identification of RANTES, MIP-1alpha and MIP-1beta as the Major HIV-Suppressive Factors Produced by CD8+ T-Cells. Science, 270:1811-1815.

Combadiere, et al. (1995). Cloning and Functional Expression of a Human Eosinophil CC Chemokine Receptor. J. Biol. Chem., 270, 16491-16494 (Note—Erratum in: J. Biol. Chem. Dec. 15, 1995;270(50):30235).

Combadiere, et al. (1996). Cloning and Functional Expression of CC CKR5, a Human Monocyte CC Chemokine Receptor Selective for MIP-1a, MIP-1β and RANTES. J. Leukos. Biol., 60:147-152.

Connor, R.I, et al., (1997). Change in Co-Receptor Use Correlates With Disease Progression in HIV-1 Infected Individuals. J. Exp. Med., 185:621-628.

Cormier, E.G., et al. (2000). Specific Interaction of CCR5 Amino-Terminal Domain Peptides Containing Sulfotyrosines With HIV-1 Envelope Glycoprotein Gp120. Proc. Natl. Acad. Sci., 97:5762-5767.

Crump, M.P., et al. (1997). Solution Structure and Basis for Functional Activity of Stromal-Cell Derived Factor-1: Disassociation of CXCR4 Activation From Binding and Inhibition of HIV-1. EMBO, 16:6996-7007.

Cruse, et al. (1995). Illustrated Dictionary of Immunology, CRC Press, Inc, Boca Raton, FL1., 143 :QR180.4.C78.

Cushman, M., et al. (1991). Preparation and Anti-HIV Activities of Aurintricarboxylic Acid Fractions and Analogues: Direct Correlation of Antiviral Potency With Molecular Weight. J. Med. Chem., 34:329-337.

Daar, E.S. (1990). High Concentrations of Recombinant Soluble CD4 Are Required to Neutralize Primary Human Immunodeficiency Virus Type 1 Isolates. Proc. Natl. Acad. Sci., 87:6574-6578.

Dalgleish, A.G., et al. (1984). The CD4 (T4) Antigen is an Essential Component of the Receptor for the AIDS Retrovirus. Nature, 312:763-766.

Dalgleish, A.G. (1995). HIV and CD26. Nature Medicine, 1:881-882.

De Rossi, A., et al. (1995). Synthetic Peptides From the Principle Neutralizating Domain of Human Immunodeficiency Virus Type 1 (HIV-1) Enhance HIV-1 Infection Through a CD4-Dependent Mechanism. Virology, 184:187-19.

Dean, M., et al. (1996). Genetic Restriction of HIV-1 Infection and Progression to AIDS by a Deletion Allele of the CKR5 Structural Gene. Science, 273:1856-1862.

De Clerq, et al. (1992). Potent and Selective Inhibition of Human Immunodeficiency Virus (HIV)-1 and HIV-2 Replication by a Class of Bicyclams Interacting With a Virus Uncoating Event. Proc. Natl. Acad. Sci., 89:5286-5290.

De Clerq, et al. (1994). Highly Potent and Selective Inhibition of Human Immunodeficiency Virus by the Bicyclam Derivative JM3100. Antimicrobial Agents and Chemotherapy, 38:668-674.

De Clerq, et al. (1995). Antiviral Therapy for Human Immunodeficiency Virus Infections. J. Clin. Microbiol. Rev., 8(2):200-239.

Deen, K.C., et al. (1988). A Soluble Form of CD4(T4) Protein Inhibits AIDS Virus Infection. Nature, 331:82-84.

Deng, H., et al. (1996). Identification of a Major Co-Receptor for Primary Isolates of HIV-1. Nature, 381:661-666.

Deng, X., et al. (1999). A Synthetic Peptide Derived From Human Immunodeficiency Virus Type 1 Gp120 Down-Regulates the Expression and Function of Chemokine Receptors CCR5 and CXCR4 in Monocytes by Activating the 7-Transmembrane GProtein-Coupled Receptor FPRL1/LXA4R. Blood, 94(4):1165-1173.

Dettin, et al. (2003). CCR5 N-Terminus Peptides Enhance X4 HIV-1 Infection by CXCR4 Up-Regulation. Biochem. Biophys. Res. Commun., 307(3):640-646.

Dikic (1996). Regulation of HIV-1 Infection by Chemokine Receptors. Acta Med. Croatica, 50:163-168.

Ditzel, et al. (1998). The CCR5 Receptor Acts as an Alloantigen in CCRΔ32 Homozygous Individuals: Identification of Chemokine and HIV-1 Blocking Human Antibodies. Proc. Natl. Acad. Sci., 95(9):5241-5245.

Donzella, G.A., et al. (1998). AMD3100, A Small Molecule Inhibitor of HIV-1 Entry Via the CXCR4 Co-Receptor. Nat. Med., 4:72-77.

Doranz, B.J., et al. (1996). A Dual-Tropic Primary HIV-1 Isolate That Uses Fusin and Beta-Chemokine Receptors CKR-5, Ckr-3 and CKR-2b as Fusion Cofactors. Cell, 85:1149-1158.

Doranz, B.J., et al. (1997). Two Distinct CCR5 Domains Can Mediate Co-Receptor Usage by Human Immunodeficiency Virus Type 1. J. Virol., 71:6305-6314.

Doranz, B.J., et al. (1997). A Small Molecule Inhibitor Directed Against the Chemokine Receptor CXCR4 Prevents Its Use as an HIV-1 Co-Receptor. J. Ex. Med., 186:1395-1400.

Dragic, T.V., et. al. (1995). Proteinase-Resistant Factors in Human Erythrocyte Membranes Mediated CD-4 Dependent Fusion With Cells Expressing Human Immunodeficiency Virus Type 1 Envelope Glycoproteins. J. Virol., 69:1013-1018.

Dragic, T.V., et al. (1996). HIV-1 Entry Into CD4+ Cells is Mediated by the Chemokine Receptor CC-CKR-5. Nature, 381:667-673.

Dragic, T.V., et al. (1998). Amino-Terminal Substitutions in the CCR5 Coreceptor Impair Gp120 Binding and Human Immunodeficiency Virus Type 1 Entry. J. Viral., 72(1):279-285.

Dragic, et al. (2000). A Binding Pocket for a Small Molecule Inhibitor of HIV-1 Entry Within the Transmembrane Helices of CCR5. Proc. Natl. Acad. Sci., 97(10):5639-5644.

Eckert, D.M., et al. (1999). Inhibiting HIV-1 Entry: Discovery of D-Peptide Inhibitors That Target the gp41 Coiled-Coil Pocket. Cell, 99:103-115.

Eugen-Olsen, J., et al. (1997). Heterozygosity for a Deletion in the CKR-5 Gene Leads to Prolonged AIDS-Free Survival and Slower CD4 T-Cell Decline in a Cohort of HIV-Seropositive Individuals. AIDS, 11:305-310.

Fahey, J.L., et al. (1992). Status of Immune-Based Therapies in HIV Infection and AIDS. Clin. Exp. Immunol., 88:1-5.

Farzan, M., et al. (1998). A Tyrosine-Rich Region in the N-Terminus of CCR5 Is Important for Human Immunodeficiency Virus Type 1 Entry and Mediates Association Between gp120 and CCR5. J. Virol., 72:1160-1164.

Farzan, M., et al. (1999). Tyrosine Sulfation of the Amino-Terminus of CCR5 Facilitates HIV-1 Entry. Cell, 96:667-676.

Farzan, M., et al. (2000). A tyrosine-sulfated peptide based on the N terminus of CCR5 interacts with a CD4-enhanced epitope of the HIV-1 gp 120 Envelope Glycoprotein and Inhibits HIV-1 Entry. J. Biol. Chem., 275:33416-33521.

Feng, et al. (1996). Abstract No. 116,21 at Keystone Symposium.

Feng, Y., et al. (1996). HIV-1 Entry Cofactor: Functional cDNA Cloning of a Seven-Transmembrane, g Protein-Coupled Receptor. Science, 272:872-877.

Ferrer, M., et al. (1999). Selection of gp-41 Mediated HIV-1 Cell Entry Inhibitors From Biased Combinatorial Libraries of Non-Natural Binding Elements. Nature. Struct. Biol., 6:953-959.

Flexner, C. and Hendrix, C. (1997). "Pharmacology of Antiretroviral Agents", in AIDS: Biology, Diagnosis, Treatment and Prevention, 4th Edition, De Vita V., et al. eds., Lippincott-Raven Publishers. pp. 479-493.

Fouts, T.R., et al. (1997). Neutralization of the Human Immunodeficiency Virus Type 1 Primary Isolate JR-FL by Human Monoclonal Antibodies Correlates With Antibody Binding to the Oligomeric Form of the Envelope Glycoprotein Complex. J. Virol., 71:2779-2785.

Fox, J.L. (1994). No Winners Against Aids. Bio/Technology, 12:128.

Fradd, F. and Mary, M.E. (1989). AIDS Vaccines: An Investor's Guide, Shearman Lehaman Hutton. p. 10:(Fig. 2).

Furuta, R.A., et al. (1998). Capture of an Early Fusion-Active Conformation of HIV-1 gp41. Nature Struct. Biol., 5(4) :276-279.

Gait, M.J and Karn, J. (1995). Progress in anti-HIV Structure Based Drug Design. TIBTECH, 13:430-438.

Gauduin, M.C., et al. (1996). Effective Ex Vivo Neutralization of Plasma HIV-1 by Recombinant Immunoglobulin Molecules. J. Virol., 70:2586-2592.

Gauduin, M.C., et al. (1997). Passive Immunization With a Human Monoclonal Antibody Protects hu-PBL-SCID Mice Against Challenge by Primary Isolates of HIV-1. Nature Medicine, 3:1389-1393.

Ghorpade A., et al. (1998). Role of the Beta-Chemokine Receptors CCR3 and CCR5 in Human Immunodeficiency Virus Type 1 Infection of Monocytes and Microglia. J. Virol, 72:3351-3361.

Golding, H., et al. (1992). LFA-1 Adhesion Molecules Are Not Involved in the Arly Stages of HIV-1 Env-Mediated Cell Membrane Fusion. AIDS Res. Hum. Retroviruses, 8:1593-1598.

Gong, J.H., et al. (1995). Antagonists of Monocyte Chemoattractant Protein 1 Identified by Modification of Functionally Critical NH2-Terminal Residues. J. Exp. Med., 181:631-640.

Gong, J.H., et al. (1996). RANTES and MCP-3 Antagonists Bind Multiple Chemokine Receptors. J. Biol. Chem., 371:10521-10527.

Grene, et al. (2001). Anti-CCR5 Antibodies in Sera of HIV-Positive Individuals. Human Immunol., 62(2):143-145.

Harrington, R.D. and Geballe, A.P. (1993). Cofactor Requirement for Human Immunodeficiency Virus Type 1 Entry Into a CD4-Expressing Human Cell Line. J. Virol., 67:5939-5947.

Hattori, T., et al. (1989). Involvement of Tryptase-Related Cellular Protease(S) in Human Immunodeficiency Virus Type 1 Infection. FEBS Letters, 248:48-52.

Haynes, B.F. (1996). Updates on the Issues of HIV Vaccine Development. Ann. Med., 28:39-41.

He, Jianglin, et al. (1997). CCR3 and CCR5 Are Co-Receptors for HIV-1 Infection of Microglia. Nature, 385:645-649.

Heath, et al. (1997). Chemokine Receptor Usage by Human Eosinophils. The Importance of CCR3 Demonstrated Using an Antagonistic Monoclonal Antibody. J. Clin. Invest., 99:178-184.

Heidenreich, et al. (1995). Application of Antisense Technology to Therapeutics. Mol. Med. Today, 1:128-133.

Hildreth, et al. (1989). Involvement of a Leukocyte Adhesion Receptor (LFA-1) in HIV-Induced Syncytium Formation. Science, 244:1075-1078.

Hill, C.M., et al. (1998). The Amino Terminus of Human CCR5 is Required for its Function as a Receptor to Diverse Human and Simian Immunodeficiency Virus Envelope Glycoproteins. Virology, 248:357-371.

Hirata, Y. (1989). Characterization of IL-6 Receptor Expression by Monoclonal and Polyclonal Antibodies. J. Immun., 2900-2906.

Howard, O.M.Z., et al. (1998). Small Molecule Inhibitor of HIV-1 Cell Fusion Blocks Chemokine Receptor-Mediated Fusion. J. Leuk. Biol., 64:6-13.

Hwang, S.S., et al. (1991). Identification of the Envelope V3 Loop as the Primary Determinant of Cell Tropism in HIV-1. Science, 253:71-74.

Jacobson, J.M., et al. (1993). Passive Immunotherapy in the Treatment of Advanced Human Immunodeficiency Virus Infection. J. Infect. Dis., 168:298-305.

Jacobson, J., et al. (1999). Results of a Phase I Trial of Single-Dose PRO 542, a Novel Inhibitor of HIV Entry. Abstracts of the 39th Interscience Conference on Antimicrobial Agents and Chemotherapy 14.

Ji, H., et al. (1999). Inhibition of Human Immunodeficiency Virus Type 1 Infectivity by the gp41 Core: Role of a Conserved Hydrophobic Cavity in Membrane Fusion. J. Virol., 73:8578-8586.

Jiang, S., et al. (1993). HIV-1 Inhibition by a Peptide. Nature, 365:113.

Jones, S.A., et al. (1997). Chemokine Antagonists That Discriminate Between Interleukin-8 Receptors. J. Biol. Chem., 272:16166-16199.

Karwowska, S., et al. (1991). Passive Immunization for the Treatment and Prevention of HIV Infection. Biotech. Therap., 2:31-48.

Katinger, H. (1994). Human Monoclonal Antibodies for Passive Immunotherapy of HIV-1. Antibiot. Chemother., 46:23-37.

Kilby, J.M., et al. (1998). Potent Suppression of HIV-1 Replication in Humans by T-20, A Peptide Inhibitor of gp41-Mediated Virus Entry. Nature Med., 4:1302-1307.

Klotman, et al. (1995). Transgenic Models of HIV-1. AIDS, 9(4):313-324.

Konigs, C., et al. (2000). Monoclonal Antibody Screening of Phage-Displayed Random Peptide Library Reveals Mimotopes of Chemokine Receptor CCR5: Implications for the Tertiary Structure of the Receptor and for an N-Terminal Binding Site for HIV-1 gp120. Eur. J. Immnol., 30(4):1162-1171.

Konishi, K., et al. (2000). Synthesis of Peptides Mimicking Chemokine Receptor CCR5 and Their Inhibitory Effects Against HIV-1 Infection. Chem. Pharm. Bull., Tokyo, 48(2):308-309.

Koup, R.A., et al. (1996). Defining Antibody Protection Against HIV-1 Transmission in Hu-PBL-Scid Mice. Immunology, 8:263-268.

Kwong, P.D. et al. (1998). Structure of an HIV gp120 Envelope Glycoprotein in Complex With the CD4 Receptor and Neutralizing Human Antibody. Nature, 393:648-659.

Laal, S., et al. (1994). Synergistic Neutralization of Human Immunodeficiency Virus Type 1 by Combinations of Human Monoclonal Antibodies. J. Virol., 68:4001-4008.

LaCasse, R.A., et al. (1999). Fusion-Competent Vaccines: Broad Neutralization of Primary Isolates of HIV. Science, 283:357-362.

Lee, B., et al. (1999). Epitope Mapping of CCR5 Reveals Multiple Conformational States and Distinct But Overlapping Structures Involved in Chemokine Coreceptor Function. J. Biol. Chem., 9617-9626.

Lehner, et al. (2001). Immunogenicity of the Extracellular Domains of C-C Chemokine Receptor 5 and the in Vitro Effects on Simian Immunodeficiency or HIV Infectivity. Journal of Immunology, 166(12):7446-7455.

Levy, J.A. (1996). Controlling HIV Pathogenesis: The Role of the Non-Cytotoxic Anti-HIV Response of CD8+ Cells. Immunology Today, 17:217-224.

Li, A., et al. (1997). Synergistic Neutralization of Chimeric SIV/HIV Type 1 Virus With Combinations of Human Anti-HIV Type 1 Envelope Monoclonal Antibodies or Hyperimmune Globulins. AIDS Res. Hum. Retroviruses, 12:647-56.

Li, A.H., et al. (1998). Synergistic Neutralization of Simian-Human Immunodeficiency Virus SHIV-vpu+ by Triple and Quadruple Combination of Human Monoclonal Antibodies and High-Titer Antihuman Immonodeficiency Virus Type 1 Immunoglobulins. J. Virol., 72:3235-3240.

Litwin, V.M., et al. (1996). Human Immunodeficiency Virus Type 1 Membrane Fusion Mediated by a Laboratory-Adapted Strain and a Primary Isolate Analyzed by Resonance Energy Transfer. J. Virol., 70(9):6437-6441.

Loetscher, M., et al. (1994). Cloning of a Human Seven-Transmembrane Domain Receptor, LESTR, That is Highly Expressed in Leukocytes. J. Biol. Chem., 269:232-237.

Mack, M., et al. (1998). Aminooxypentane-RANTES Induces CCR5 Internalization But Inhibits Recycling: A Novel Inhibitory Mechanisms of HIV Infectivity. J. Ex. Med., 187:1215-1224.

Mackay, C.R. (1996). Chemokine Receptors and T Cell Chemotaxis. J. Exp. Med., 84:799-802.

Maddon, P.J., et al. (1986). The T4 Gene Encodes the AIDS Virus Receptor and is Expressed in the Immune System and the Brain. Cell, 47:333-348.

Markosyan, R.M., et al. (2002). The Mechanism of Inhibition of HIV-1 Entry Env-Mediated Cell-Cell Fusion by Recombinant Cores of gp41 Ectodomain. Virology, 302:174-184.

McKnight, A.D., et al. (1997). Inhibition of Human Immunodeficiency Virus Fusion by a Monoclonal Antibody to a Coreceptor (CXCR4) is Both Cell Type and Virus Strain Dependent. J. Virol., 71:1692-1696.

Mellors, J.W. (1996). Closing in on Human Immunodeficiency Virus-1. Nature Medicine, 2(3):274-275.

Mohan, P., et al. (1992). Sulfonic Acid Polymers as a New of Class of Human Immunodeficiency Virus Inhibitors. Antiviral Res., 18:139-150.

Moser, B., et al. (1993). Interleukin-8 Antagonists Generated by N-Terminal Modification. J. Biol. Chem., 268:7125-7128.

Mosier, D.E. (1990). Immunodeficient Mice Xenografted With Human Lymphoid Cells: New Models for In-Vivo Studies of Human Immunobiology and Infectious Diseases. J. Clin. Immuno., 10(4):185-191.

Nagasawa, et al. (1994). Molecular Cloning and Structure a Pre-B-Cell Growth-Stimulating Factor. Proc. Natl. Acad. Sci., 91:2305-2309.

Nagashima, K.A., et al. (2001). Human Immunodeficiency Virus Virus Type 1 Entry Inhibitors PRO 542 and T-20 are Potently in Blocking Virus-Cell and Cell-Cell Fusion. J. Infect. Dis., 183:1121-1125.

Nakano, T., et al. (1995). Vascular smooth muscle cell-derived, Gla-containing growth-potentiating factor for Ca2+ mobilizing growth factors. J. Biol. Chem., 270(11):5702-5705.

Neote, et al. (1993). Molecular cloning, functional expression, and signaling characteristics of a C-C chemokine receptor. Cell, 72:415-425.

Oberg, B and Vrang, L. (1990). Screening for new agents. Eur. J. Clin. Microbiol. Infect. Dis., 9(7):466-471.

Oberlin, E., et al. (1996). The CXC Chemokine SDF-1 is the Ligand for LESTR/fusion and prevents infection by T-cell-line-adapted HIV-1. Nature, 382: 833-835.

Oellerich, M., (1984). Enzyme-Immunoassay: A Review. J. Clin. Chem. Clin. Biochem., 22(12):895-904.

Olson, et al., (1999). Differential Inhibition of Human Immunodeficiency Virus Type 1 Fusion, gp120 Binding and CC-chemokine Activity of Monoclonal Antibodies to CCR5. J. Virol., 73:4145-4155.

Opperman, (2004). Chemokine Receptor CCR5: Insights Into Structure, Function, and Regulation. Cell. Signal., 16:1201-1210.

Parren, et al. (2001). Antibody Protects Macaques Against Vaginal Challenge With a Pathogenic R5 Simian/Human Immunodeficiency Virus at Serum Levels Giving Complete Neutralization in Vitro. J. Virol., 75:8340-8347.

Partidos, C., et al. (1992). The Effect of Orientation of Epitopes on the Immunogenicty of Chimeric Synthetic Peptides Representing Measles Virus Protein Sequences. Molecular Immunology, 29(5):651-658.

Poignard, P., et al. (1999). Neutralizing Antibodies Have Limited Effects on the Control of Established HIV-1 Infection In-Vivo. Immunity, 10:431-438.

Posner, M.R., et al. (1993). Neutralization of HIV-1 by F105, a Human Monoclonal Antibody to the CD4 Binding Site of gp120. J. Acq. Immune Defic. Synd., 6:7-14.

Power, et al. (1995). Molecular Cloning and Functional Expression of a Novel CC Chemokine Receptor Cdna From a Human Basophilic Cell Line. J. Biol. Chem., 270:1811-1815.

Proudfoot, et al. (1996). Extension of Recombinant Human RANTES by the Retention of the Initiating Methionine Produces a Potent Antagonist. J. Biol. Chem., 271:2599-2603.

Proudfoot, et, al. (1999). Chemokine Receptors: Future Therapeutic Targets for HIV. Biochem. Pharmacol., 57:451-463.

Proudfoot, et al. (2000). The Strategy of Blocking the Chemokine System to Combat Disease. Immunol. Rev., 177:246-256.

Queen, et al. (1989). A Humanized Antibody That Binds to Interleukin 2 Receptor. Proc. Natl. Acad. Sci, 86:10029-10033.

Rabut, G.E., et al. (1991). Alanine Substitutions of Polar and Nonpolar Residues in the Amino-Terminal Domain of CCR5 Differently Impair Entry of Macrophage and Dualtropic Isolates of Human Immunodeficiency Virus Type 1. J. Virol., 72:3464-3468.

Raport, C.J., et al. (1996). Molecular Cloning and Functional Characterization of a Novel Human CC-Chemokine Receptor (CCR5) for RANTES, MIP-1β, and MIP-1a. J. Biol. Chem., 271:1761-1766.

Raport, C.J., et al. (1996). New Members of the Chemokine Receptor Gene Family. Journal of Leukocyte Biology, 59:18-23.

Raport, C.J., et al. (1996). AAC50598 submitted to NCBI on Apr. 12, 1996 (CC Chemokine Receptor 5 sequence).

Richman, D.D. (1996). Antiretroviral Drug-Resistance: Mechanisms, Pathogenesis, Clinical Significance. Antivir. Chemother., 4:383-395.

Rodriguez, G., et al. (1995). Mediation of Human Immunodeficiency Virus Type 1 Binding by Interaction of Cel Surface Heparin Sulfate Proteoglycans With V3 Region of Envelope gp120-gp41. J. Virol., 69:2233-2239.

Rucker, et al. (1996). Regions in Beta-Chemokine Receptors and CCR2b That Determine HIV-1 Cofactor Specificity. Cell, 87:437-446.

Ruffing, et al. (1998). CCR5 Has an Expanded Ligand-Binding Repertoire and is the Primary Receptor Used by MCP-2 on Activated T-Calls. Cell. Immunol., 160:160-168.

Rudikoff, et al. (1982). Single Amino Acid Substitution Altering Antigen-Binding Specificity. Proc. Natl. Acad. Sci., 79:1979-1983.

Samson, M., et al. (1996). Molecular Cloning and Functional Expression of a New Human CC-Chemokine Receptor Gene. Biochem., 35:3362-3367.

Sandberg, J. (1995). Developmental Pharmacology and Toxicology of Anti-HIV Therapeutic Agents: Dideoxynucleosides. FASEB J., 9:1157-1163.

Sato, et al. (1992). Anti-Cd7 Reagents Inhibit HIV-1 Induced Syncytium Formation. International Conference on AIDS, 81. PA5 PoA 2017.

Sato, et al. (1994). Identification of CD7 Glycoprotein as an Accessory Molecule in HIV-1 Mediated Syncytium Formation and Cell Free Infection. J. Immunol., 152:5142-5152.

Sato, et al. (1995). A Simple and Rapid Method for Preliminary Evaluation of in Vivo Efficacy of Anti-HIV Compounds in Mice. Antivir. Res., 27:151-163.

Scarlatti, et al. (1997). In Vivo Evolution of HIV-1 Co-Receptor Usage and Sensitivity to Chemokine-Mediated Suppression. Nature Medicine, 3(11):1259-1265.

Schanberg, et al. (1995). Characterization of Human CD7 Transgenic Mice. J. of Immunol., 155:2407-2418.

Schols, D., et al. (1990). Dextran sulfate and other olyanionic anti-HIV compounds specifically interact with the viral gp120 Glycoprotein Expressed by T-Cells Persistently Infected With HIV-1. Virology, 175:556-561.

Schols, D., et al. (1991). Selective Inhibitory Activity of Polyhydroxycarboxylates Derived From Phenolic Compounds Against Human Immunodeficiency Virus Replication. J. Acq. Immune Defic. Synd., 4:677-685.

Schols, D., et al. (1999). CD26-Processed RANTES(3-68), But Not Intact RANTES, Has Potent Anti-HIV-1 Activity. Antiviral Res., 30:175-187.

Simmons, G., et al. (1997). Potent Inhibition of HIV-1 Infectivity in Macropages and Lymphocytes by a Novel CCR5 Antagonist. Science, 276:276-279.

Sommerfelt, M.A., et al. (1995). Intercellular Adhesion Molecule 3, a Candidate Human Immunodeficiency Virus Type 1 Co-Receptor on Lymphoid and Monocytoid Cells. J. Gen. Virol., 76:1345-1352.

Steinberger, P., et al. (2000). Generation and Characterization of a Recombinant Human CCR5-Specific Antibody. J. Biol. Chem., 275:36073-36078.

Stewart, G.J. (1997). Increased Frequency of CCR-5Δ32 Heterozygotes Among Long-Term Non-Progressors With HIV-1 Infection. AIDS, 11:1833-1838.

Strizki, J.M., et al. (1997). A Monoclonal Antibody (12G5) Directed Against CXCR4 Inhibits Infection With the Dual-Tropic Human Immunodeficiency Virus Type 1 Isolates HIV-1 89.6 but not the T-Tropic Isolate HIV-1 HxB. J. Virol., 71:5678-5683.

Su, et al. (1996). Preparation of Specific Polyclonal Antibodies to a C-C Chemokine Receptor, CCR1, and Determination of CCR1 Expression on Various Types of Leukocytes. J. Leukos. Biol., 60:658-666.

Thali, M., et al. (1992). Cooperativity of Neutralizing Antibodies Directed Against the VS and CD4 Binding Regions of the Human Immunodeficiency Virus gp120 Envelope Glycoprotein. J. Acq. Immune. Defic. Synd., 5:591-599.

Tilley, S.A., et al. (1991). Potent Neutralization of HIV-1 by Human and Chimpanzee Monoclonal Antibodies Directed Against Three Distinct Epitope Clusters of gp120. Sixieme Colloque Des Cent Gardes., 211-216.

Tremblay, et al. (2000). Strong in Vitro Synergy Observed Between the Fusion Inhibitor T-20 and a CXCR4 Blocker AMD-3100. Feb. 7, 2000 Conference on Retroviruses and Opportunistic Infections, abstract 500.

Tremblay, et al. (1999). Strong in Vitro Synergy Between the Fusion Inhibitor T-20 and the CXCR4 Blocker AMD-3100. Journal of Acquired Immune Deficiency Syndromes, 25(2):99-102.

Trkola, A., et al. (2001). Potent, Broad-Spectrum Inhibition of Human Immunodeficiency Virus Type 1 by the CCR5 Monoclonal Antibody PRO 140. J. Virol., 75:579-588.

Trkola, A., et al. (1999). Cross-Glade Neutralization of Primary Isolates of Human Immunodeficiency Virus Type 1 by Human Monoclonal Antibodies and Tetrameric CD4-IgG. J. Virol., 73(5):4145-4155.

Trkola, A., et al. (1996). CD-4 Dependent, Antibody Sensitive Interactions Between HIV-1 and Its Co-Receptor CCR-5. Nature, 384:184-187.

Trkola, A., et al. (1998). Neutralization Sensitivity of Human Immunodeficiency Virus Type 1 Primary Isolates to Antibodies and CD40 based Reagents is Independent of Coreceptor Usage. J. Virol., 72:1876-1885.

Tulip, W.R., et al. (1992). Crystal Structures of Two Mutant Neraminidase-Antibody Complexes With Amino Acid Substitutions in the Interface. J. Mol. Biol., 227:149-159.

Valentin, et al. (1990). The Leukocyte Adhesion Glycoprotein CD18 Participates in HIV Induced Syncyia Formation in Monocytoid and T Cells. J. of Immunology, 144:934-937.

Valenzuela, A., et al. (1997). Neutralizing Antibodies Against the V3 Loop of Human Immunodeficiency Virus Type 1 Block the CD4-Dependent and Independent Binding of Virus to Cells. J. Virol., 71(11):8289-8298.

Vijh-Warrier, S., Pinter, A., Honnen, W.J., and Tilley, S.A. (1996). Synergistic Neutralization of Human Immunodeficiency virus Type 1 by a Chimpanzee Monoclonal Antibody Against the V2 Domain of gp120 in Combination With Monoclonal Antibodies Against the V3 Loop and the CD4-Binding Site. J. Virol., 70:4466-4473.

Vila-Coro, et al. (2000). HIV-1 Infection Through the CCR5 Receptor is Blocked by Receptor Dimerization. Proc. Natl. Acad. Sci., 97(7):3388-3393.

Vita, C., et al. (1999). Rational Engineering of a Mini-Protein That Reproduces the Core of the CD4 Site Interacting With HIV-1 Envelope Glycoprotein. Proc. Natl. Acad. Sci., 96:13091-13096.

Wang, et al. (1994). Deletion of T Lymphocytes in Human CD4 Transgenic Mice Induced by HIV-gp120 and gp120-Specific Antibodies From AIDS Patients. Eur. J. Immunol., 24:1553-1557.

Wells, T.N.C., et al. (1996). Selectivity and Antagonism Chemokine Receptors. Journal of Leukocyte Biology, 59:53-60.

Wild, C., et al. (1992). A Synthetic Peptide Inhibitor of Human Immunodeficiency Virus Replication: Correlation Between Solution Structure and Viral Inhibition. Proc. Natl. Acad. Sci., 89:10537-10541.

Wild, C., et al. (1993). A synthetic peptide from HIV-1 Gp41 is a Potent Inhibitor of Virus Mediated Cell-Cell Fusion. AIDS Res. Hum. Retroviruses, 9:1051-1053.

Wild, C., et al. (1994). Peptides Corresponding to a Predictive Alpha-Helical Domain of Human Immunodeficiency Virus Type 1 gp41 are Potent Inhibitors of Virus Infection. Proc. Natl. Acad. Sci., 91:9770-9774.

Wild, C., et al. (1995). The Inhibitory Activity of an HIV Type 1 Peptide Correlates With its Ability to Interact With a Leucine Zipper Structure. AIDS Res. Hum. Retroviruses, 11:323-325.

Wu, et al. (1997). CCR5 Levels and Expression Pattern Correlate With Infectability by Macrophagetropic HIV-1 in Vitro. J. Exp. Med., 185(9):1681-1691.

Wu, et al. (1997). Interaction of Chemokine Receptor CCR5 With its Ligands: Multiple Domains for HIV-1 gp120 Binding a Single Domain for Chemokine Binding. J. Exper. Med., 186(8):1373-1381.

Wu, L., et al. (1996). CD4-Induced Interaction of Primary HIV-1 gp120 Glycoproteins With the Chemokine Receptor CCR-5. Nature, 384:179-183.

Yamagami, et al. (1994). cDNA Cloning and Functional Expression of Human Monocyte Chemoattractant Protein 1 Receptor. Biochem. Biophys. Res. Commun., 212:1156-1162.

Yarchoan, R. and Broder, S. (1992). Correlations Between the in Vitro and the in Vivo Activity of Anti-HIV Agents: Implications for Future Drug Development. J. Enzyme Inhibit., 6:99-11.

Ylisastigui, L., et al. (1998). Synthetic Full Length and Truncated RANTES Inhibit HIV-1 Infection or Primary Macrophages. AIDS, 12:977-984.

Zhang, Y.J., et al. (1994). Structure / Activity Analysis of Human Monocyte Chemoattractant Protein-1 (MCP-1) by Mutagenesis. J. Biol. Chem., 269:15918-15924.

PCT International Search Report issued Jun. 9, 1997 for International Application Publication No. WO 97/26009.

PCT International Search Report issued Jul. 5, 1997 for International Application Publication No. WO 98/56421.

PCT International Search Report issued Sep. 3, 1997 International Application Publication No. WO 97/47319.

PCT International Search Report issued Sep. 12, 1998 International Application Publication No. WO 98/56421.

PCT International Search Report issued Sep. 3, 1997 for International Application Publication No. WO 97/47318.

PCT International Search Report issued Jun. 7, 2000 for Application Publication No. WO 00/35409.

PCT International Search Report issued Aug. 13, 2003 for Application Publication No. WO 03/072766.

PCT International Search Report issued Apr. 23, 2002 for International Application Publication No. WO 02/22077.

PCT International Search Report issued Jul. 31, 2003 for International Application Publication No. WO 02/083172.

PCT International Preliminary Examination Report issued Jan. 27, 2000 for International Application Publication No. WO 98/56421.

PCT International Preliminary Examination Report issued Jul. 10, 1998 for International Application Publication No. WO 97/37005.

PCT International Preliminary Examination Report issued Oct. 16, 1999 for International Application Publication No. WO 97/47319.

PCT International Preliminary Examination Report issued Sep. 28, 2005 for International Application Publication No. WO 03/072766.

PCT International Preliminary Examination Report issued Apr. 5, 2006 for International Application Publication No. WO 03/072766.

PCT International Preliminary Examination Report issued Feb. 15, 2001 for International Application Publication No. WO 00/35409.

PCT International Preliminary Examination Report issued Dec. 24, 2003 for International Application Publication No. WO 02/083172.

PCT Written Opinion issued May 25, 2005 in connection with International Application Publication No. WO 03/072766.

European Supplementary Partial Search Report issued Sep. 27, 2004 for European Application No.

European Supplementary Partial Search Report issued Feb. 19, 2003 for European Patent Application No. 98931261.6.

European Supplementary Partial Search Report issued Aug. 26, 2004 for European Patent Application No. 97930120.7.

European Supplementary Partial Search Report issued Nov. 8, 2004 for European Patent Application No. 97930120.7.

European Supplementary Search Report issued Apr. 21, 2006 European Application No. 03713632.2.

European Supplementary Search Report issued Mar. 6, 2002 European Patent Application No. 97917856.3.

European Supplementary Search Report issued Apr. 27, 2006 European Patent Application No. 01970984.9.

European Patent Office Communication issued Nov. 11, 2004 in connection with European Patent Application No. 97930120.7.

Max, E. "Immunoglobulins: Molecular Genetics" in Fundamental Imunology, 6th edition. W.E. Paul, ed., Lippincott-Raven Publishers, Philadelphia, 2008 pp. 192-236.

Nelson et al. "Efficacy and Safety of Maraviroc plus Optimized Background Therapy in Viremic, ART-experienced Patients Infected with CCR5-tropic HIV-1 in Europe, Australia, and North America: 24-Week results," 14th Annual Conference on Retroviruses and Opportunistic Infections. Feb. 28, 2007. Abstract #104aLB.

Schroeder et al. (2008) "Immunoglobulins: Structure and Function," Lippincott Williams & Wilkins:Maryland, Fundamental Immunology, 6th Edition, Chapter 4, pp. 125-151.

Combadiere, C. et al. (1995) Additions and Corrections to "Cloning and functional expression of a human eosinophil CC chemokine receptor," J. Biol. Chem. 270(28) 16491-16494.

Jun. 18, 2008 Communication including Partial European Search Report in connection with European Patent Application No. 07 01 4859.8.

Sep. 19, 2008 Final Office Action issued in connection with U.S. Appl. No. 09/460,216.

Jul. 9, 2008 Office Action issued in connection with U.S. Appl. No. 11/258,963.

Jul. 1, 2008 Office Action issued in connection with U.S. Appl. No. 11/581,944.

Jan. 9, 2008 Final Office Action issued in connection with U.S. Appl. No. 11/258,963.

May 29, 2008 Office Action issued in connection with U.S. Appl. No. 11/259,540.

Nov. 19, 2007 Final Office Action issued in connection with U.S. Appl. No. 09/904,356.

Apr. 9, 2008 Office Action issued in connection with U.S. Appl. No. 11/451,707.

Nov. 2, 2007 Office Action issued in connection with U.S. Appl. No. 11/805,573.

Sep. 21, 2007 Notice of Allowability issued in connection with U.S. Appl. No. 11/544,346, now U.S. Patent No. 7,345,153.

Mar. 11, 2008 Office Action issued in connection with U.S. Appl. No. 09/888,938.

May 31, 2007 Office Action issued in connection with U.S. Appl. No. 09/888,938.

Oct. 4, 2007 Office Action issued in connection with U.S. Appl. No. 11/175,815.

Nov. 16, 2007 Office Action issued in connection with U.S. Appl. No. 09/460,216.

Sep. 12, 2007 Final Office Action issued in connection with U.S. Appl. No. 11/400,497.

Apr. 3, 2008 Office Action issued in connection with U.S. Appl. No. 11/520,556.

Jan. 9, 2008 Office Action issued in connection with U.S. Appl. No. 11/259,540.

May 22, 2008 Office Action issued in connection with U.S. Appl. No. 11/491,330.

Aug. 5, 2008 Final Office Action issued in connection with U.S. Appl. No. 11/175,815.

Aug. 19, 2008 Office Action issued in connection with U.S. Appl. No. 11/804,746.

Aug. 21, 2008 Office Action issued in connection with U.S. Appl. No. 09/904,356.

Sep. 11, 2008 Office Action issued in connection with U.S. Appl. No. 11/805,573.

Apr. 9, 2008 Office Action issued in connection with U.S. Appl. No. 11/316,078.

May 14, 2008 Office Action issued in connection with U.S. Appl. No. 11/400,497.

Notification of Transmittal of the International Search Report and the Written Opinion of the International Searching Authority, or the Declaration issued Jul. 25, 2008 in connection with PCT International Application No. PCT/US06/28565.

Notification of Transmittal of the International Search Report and the Written Opinion of the International Searching Authority, or the Declaration issued Aug. 15, 2008 in connection with PCT International Application No. PCT/US08/05564.

May 15, 2008 Office Action issued in connection with U.S. Appl. No. 11/581,945.

Sep. 16, 2008 Communication including a May 29, 2008 Extended European Search report in connection with European Patent Application No. 07014859.8.

Oct. 2, 2008 Communication Pursuant to Article 94(3) EPC and Result of Consultation issued in connection with European Patent Application No. 01970984.9.

Office Action issued Nov. 10, 2008 in connection with U.S. Appl. No. 11/400,497.

Office Action issued Dec. 12, 2008 in connection with U.S. Appl. No. 11/491,330.

Final Office Action issued Dec. 31, 2008 in connection with U.S. Appl. No. 11/581,945.

Final Office Action issued Jan. 9, 2009 in connection with U.S. Appl. No. 11/451,707.

Decision to Refuse European Patent Application issued Nov. 26, 2007 by the European Patent Office in European Patent Application No. 97917856.3.

Apr. 7, 2008 Statement Setting Out Grounds of Appeal (Article 108 EPC) filed by applicants in connection with European Application No. 97917856.3.

Final Office Action issued Jan. 27, 2009 in connection with U.S. Appl. No. 11/520,556.

Final Office Action issued Jan. 27, 2009 in connection with U.S. Appl. No. 11/259,540.

Simmons, G. et al. (1996) "Primary, syncytium-inducing human immunodeficiency virus type 1 isolates are dual-tropic and most can use either Lestr or CCR5 as coreceptors for virus entry," J. Virol. 70(12):8355-8360.

Valentin, A. et al. (1994) "Dual tropism for macrophages and lymphocytes is a common feature of primary human immunodeficiency virus type 1 and 2 isolates," J. Virol. 68(10):6684-6689.

Final Office Action issued Feb. 4, 2009 in connection with U.S. Appl. No. 11/316,078.

Notice of Allowance issued Aug. 25, 2010 in connection with U.S. Appl. No. 09/460,216; and.

Notice of Allowance issued Sep. 2, 2010 in connection with U.S. Appl. No. 09/904,356.

* cited by examiner

Anti-CCR5 mAbs Inhibit gp120/CCR5 Binding

CCR5 CHEMOKINE RECEPTOR-SPECIFIC MONOCLONAL ANTIBODIES CAPABLE OF INHIBITING HIV-1 CELL FUSION This application is a continuation of U.S. Ser. No. 09/460,216, filed Dec. 13, 1999, which is a continuation of PCT International Application No. PCT/98/12331, filed Jun. 12, 1998, which is a continuation-in-part of U.S. Ser. No. 08/876,078, filed Jun. 13, 1997 now U.S. Pat. No. 6,107,019, a continuation-in-part of U.S. Ser. No. 08/831,823, filed Apr. 2, 1997 now U.S. Pat. No. 6,344,545, claiming benefit of U.S. Provisional Nos. 60/019,715, filed Jun. 14, 1996 and 60/014,532, filed Apr. 2, 1996, the contents of each of which is hereby incorporated by reference into this application.

Throughout this application, various references are referred to within parentheses. Disclosures of these publications in their entireties are hereby incorporated by reference into this application to more fully describe the state of the art to which this invention pertains. Full bibliographic citation for these references may be found at the end of each series of experiments.

BACKGROUND OF THE INVENTION

Chemokines are a family of related soluble proteins of molecular weight between 8 and 10 KDa, secreted by lymphocytes and other cells, which bind receptors on target cell surfaces resulting in the activation and mobilization of leukocytes, for example in the inflammatory process. Recently, Cocchi et al. demonstrated that the chemokines RANTES, MIP-1α and MIP-1β are factors produced by CD8$^+$ T lymphocytes which inhibit infection by macrophage-tropic primary isolates of HIV-1, but not infection by laboratory-adapted strains of the virus (1). These chemokines are members of the C-C group of chemokines, so named because they have adjacent cysteine residues, unlike the C-X-C group which has a single amino acid separating these residues (2). While Cocchi et al. found that expression of HIV-1 RNA was suppressed by treatment with the chemokines, they did not identify the site of action of these molecules.

A resonance energy transfer (RET) assay of HIV-1 envelope glycoprotein-mediated membrane fusion was used to determine whether fusion mediated by the envelope glycoprotein from the primary macrophage-tropic isolate of HIV-$1_{JR\text{-}FL}$ would be specifically inhibited by chemokines, when compared with fusion mediated by the envelope glycoprotein from the laboratory-adapted T lymphotropic strain HIV-$1_{LAI}$. As described below, it was demonstrated that this is indeed the case. This demonstrates that some chemokine receptors are fusion accessory molecules required for HIV-1 infection. Previous studies have indicated that unidentified cell surface molecules are required for virus entry in addition to the HIV-1 receptor, CD4. While CD4 is required for HIV-1 attachment, the accessory molecules are required for the membrane fusion step of entry. These accessory molecules are generally expressed only on human cells, so HIV-1 does not infect non-human CD4$^+$ cells (3-6). Moreover it is possible to complement non-human CD4$^+$ cells by fusing them (using polyethylene glycol) with CD4$^-$ human cells, resulting in a heterokaryon which is a competent target for HIV-1 envelope-mediated membrane fusion (7, 8). These studies have been performed using laboratory-adapted T lymphotropic strains of the virus.

In some cases, it appears that fusion accessory molecules are found on a subset of human CD4$^+$ cells and are required for infection by HIV-1 isolates with particular tropisms. For example, macrophage-tropic primary strains of HIV-1 such as HIV-$1_{JR\text{-}FL}$ may have different requirements for accessory molecules compared with laboratory-adapted T lymphotropic strains such as HIV-$1_{LAI}$. This phenomenon may explain differences in tropism between HIV-1 strains.

The current invention comprises a series of new therapeutics for HIV-1 infection. It was demonstrated for the first time that chemokines act at the fusion step of HIV-1 entry and specifically inhibit membrane fusion mediated by the envelope glycoprotein of primary macrophage-tropic primary viral isolates, not laboratory-adapted T lymphotrophic strains of the virus. Primary macrophage-tropic isolates of the virus are of particular importance since they are the strains usually involved in virus transmission, and may have particular importance in the pathogenesis of HIV-1 infection.

These results were obtained using a resonance energy transfer (RET) assay of HIV-1 envelope-mediated membrane fusion. Moreover, this assay is used to identify non-chemokines, including fragments of chemokines and modified chemokines, that inhibit HIV-1 envelope glycoprotein-mediated membrane fusion and thereby neutralize the virus, yet do not induce an inflammatory response.

SUMMARY OF THE INVENTION

This invention provides a method for inhibiting fusion of HIV-1 to CD4$^+$ cells which comprises contacting CD$^+$4 cells with a non-chemokine agent capable of binding to a chemokine receptor in an amount and under conditions such that fusion of HIV-1 to the CD4$^+$ cells is inhibited.

This invention also provides a method for inhibiting HIV-1 infection of CD4$^+$ cells which comprises contacting CD4$^+$ cells with a non-chemokine agent capable of binding to a chemokine receptor in an amount and under conditions such that fusion of HIV-1 to the CD4$^+$ cells is inhibited, thereby inhibiting the HIV-1 infection.

This invention further provides non-chemokine agents capable of binding to the chemokine receptor and inhibiting fusion of HIV-1 to CD4$^+$ cells.

This invention provides an agent which is capable of binding to fusin and inhibiting infection. In an embodiment, the agent is an oligopeptide. In another embodiment, the agent is an polypeptide. In still another embodiment, the agent is an antibody or a portion of an antibody. In a separate embodiment, the agent is a nonypeptidyl agent.

In addition, this invention provides pharmaceutical compositions comprising an amount of the above non-chemokine agents or agents capable of binding to fusin effective to inhibit fusion of HIV-1 to CD4$^+$ cells and a pharmaceutically acceptable carrier.

This invention provides a composition of matter capable of binding to the chemokine receptor and inhibiting fusion of HIV-1 to CD4$^+$ cells comprising a non-chemokine agent linked to a ligand capable of binding to a cell surface receptor of the CD4$^+$ cells other than the chemokine receptor such that the binding of the non-chemokine agent to the chemokine receptor does not prevent the binding of the ligand to the other receptor.

This invention also provides a pharmaceutical composition comprising an amount of the above-described composition of matter effective to inhibit fusion of HIV-1 to CD4$^+$ cells and a pharmaceutically acceptable carrier.

This invention provides a composition of matter capable of binding to the chemokine receptor and inhibiting fusion of HIV-1 to CD4$^+$ cells comprising a non-chemokine agent linked to a compound capable of increasing the in vivo half-life of the non-chemokine agent.

This invention also provides a pharmaceutical composition comprising an amount of a composition of matter comprising a non-chemokine agent linked to a compound capable of increasing the in viva half-life of the non-chemokine agent effective to inhibit fusion of HIV-1 to CD4+ cells and a pharmaceutically acceptable carrier.

This invention provide methods for reducing the likelihood of HIV-1 infection in a subject comprising administering an above-described pharmaceutical composition to the subject. This invention also provides methods for treating HIV-1 infection in a subject comprising administering an above-described pharmaceutical composition to the subject.

This invention also provides methods for determining whether a non-chemokine agent is capable of inhibiting the fusion of HIV-1 to a CD4+ cell which comprise: (a) contacting (i) a CD4+ cell which is labeled with a first dye and (ii) a cell expressing the HIV-1 envelope glycoprotein on its surface which is labeled with a second dye, in the presence of an excess of the agent under conditions permitting the fusion of the CD4+ cell to the cell expressing the HIV-1 envelope glycoprotein on its surface in the absence of the agent, the first and second dyes being selected so as to allow resonance energy transfer between the dyes; (b) exposing the product of step (a) to conditions which would result in resonance energy transfer if fusion has occurred; and (c) determining whether there is a reduction of resonance energy transfer, when compared with the resonance energy transfer in the absence of the agent, a decrease in transfer indicating that the agent is capable of inhibiting fusion of HIV-1 to CD4+ cells.

% RET resulting from the fusion of PM1 cells and HeLa-env$_{JR-FL}$ (■) or HeLa-env$_{LAI}$ (♦) was measured in the presence and absence of recombinant human chemokines at a range of concentrations: RANTES (80-2.5 ng/ml), MIP-1α (400-12.5 ng/ml) and MIP-1β (200-6.25 ng/ml), as indicated. Chemokines were added simultaneously with the cells at the initiation of a four hour incubation. Data are representative of more than three independent experiments which were run in duplicate. The percent inhibition of RET is defined as follows:

% Inhibition=100·[(Max *RET*–Min *RET*)–(Exp *RET*–Min *RET*)]/(Max *RET*–Min *RET*)

where Max RET is the % RET value obtained at four hours with HeLa-env cells and CD4-expressing cells in the absence of an inhibitory compound; Exp RET is the % RET value obtained for the same cell combination in the presence of an inhibitory compound and Min RET is the background FRET value obtained using HeLa cells in place of HeLa envelope-expressing cells.

Figure 2A:
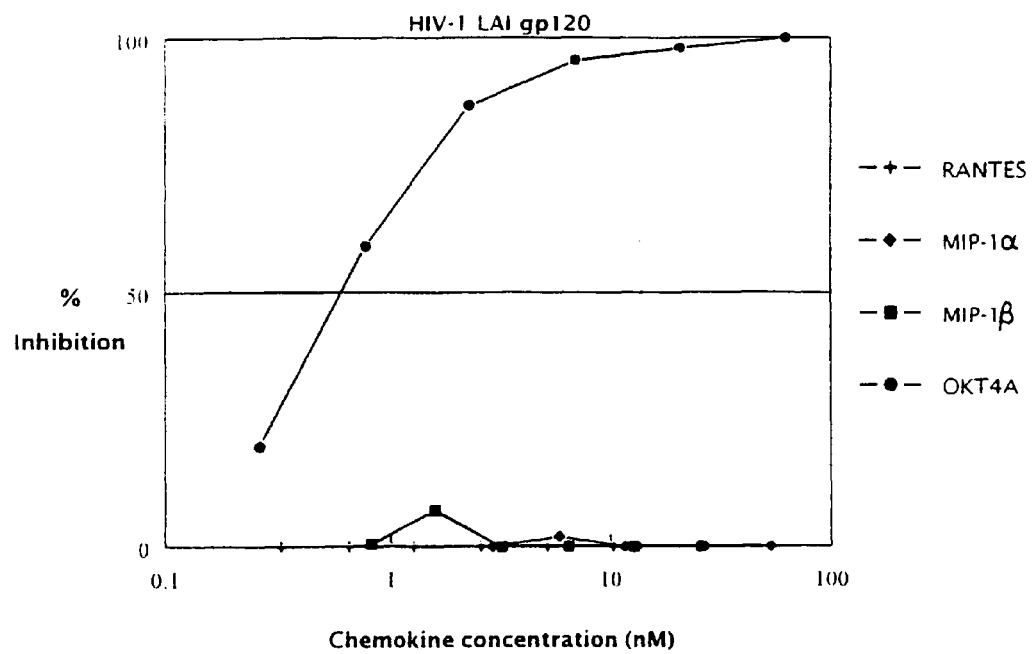
Figure 2B:
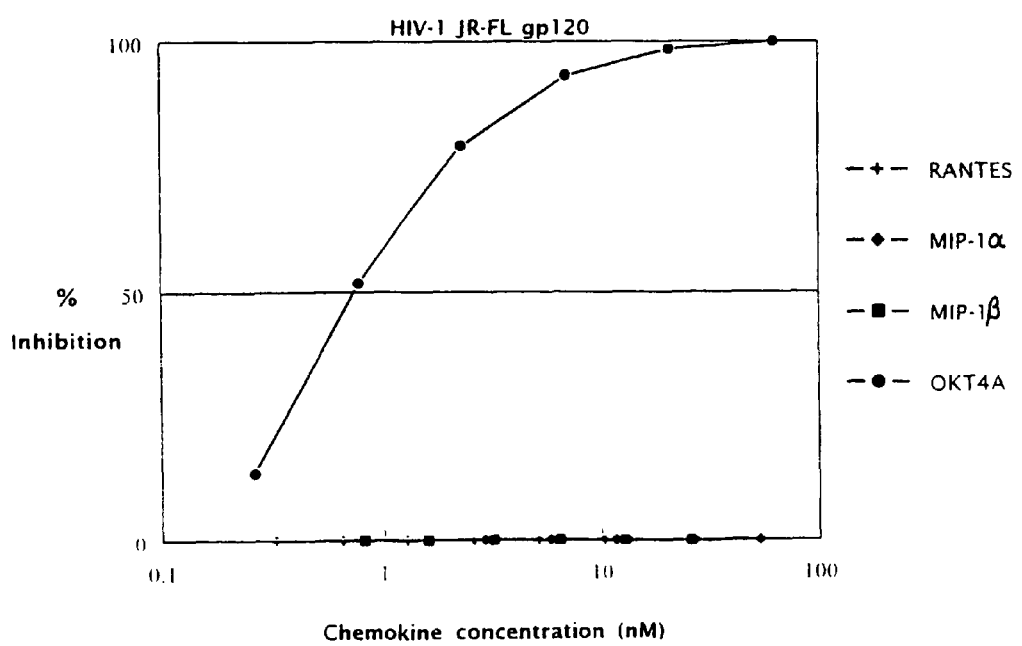

FIG. 2. CD4:HIV-1 gp120 binding in the presence of human chemokines.

Figure 1A:
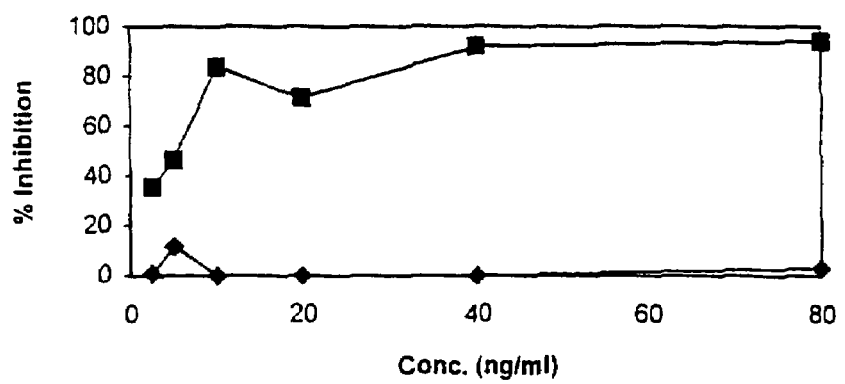
FIG. 1. Membrane fusion mediated by the HIV-1$_{JR-FL}$ envelope glycoprotein is inhibited by RANTES, MIP-1α and MIP-1β.
Figure 1B:
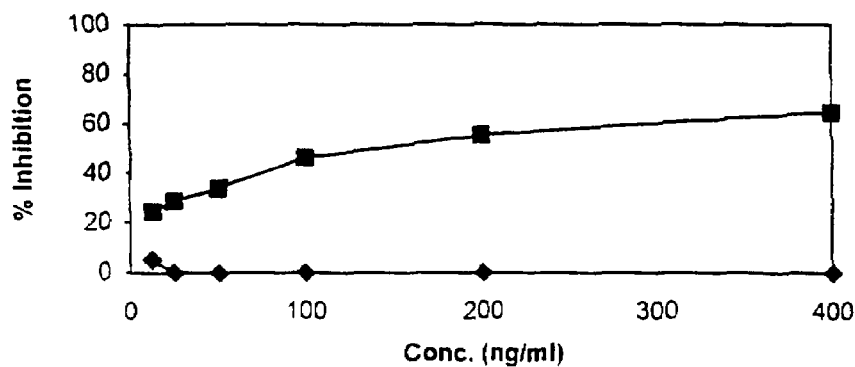
Figure 1C:
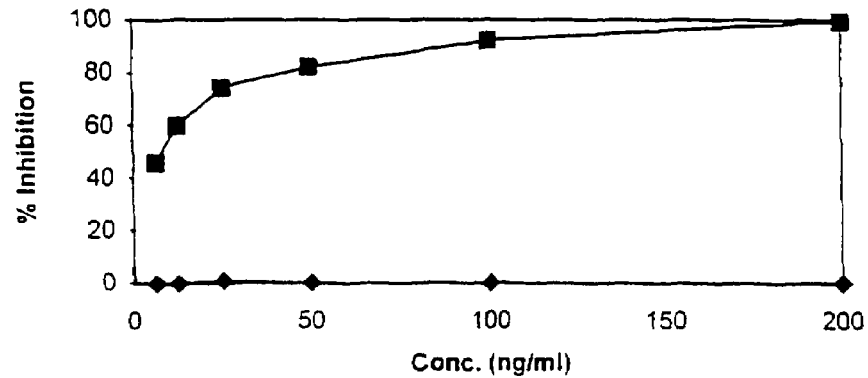

The binding of soluble human CD4 to HIV-1$_{LAI}$ and HIV-1$_{JR-FL}$ gp120 was determined in an ELISA assay in the presence and absence of the monoclonal antibody OKT4A or recombinant human chemokines at a range of concentrations, identical to those used in the RET inhibition studies of FIG. 1: OKT4A (62-0.3 nM), RANTES (10.3-0.3 nM), MIP-1α (53.3-2.9 nM), and MIP-1 (25.6-0.8 nM) Inhibitors were added simultaneously with biotinylated HIV-1 gp120 to soluble CD4 coated microtiter plates (Dynatech Laboratories, Inc., Chantilly, Va.). Following a two hour incubation at room temperature and extensive washing, an incubation with streptavidin-horseradish peroxidase was performed for one hour at room temperature. Following additional washes, substrate was added and the OD at 492 nm determined in an ELISA plate reader. Data are representative of two independent experiments which were run in quadruplicate.

FIG. 3. Specificity. time course and stage of β-chemokine inhibition of HIV-1 replication.

(a) PM1 cells (1×10$^6$) were preincubated with RANTES+MIP-1α+MIP-1β (R/Mα/Mβ; 100 ng/ml of each) for 24 h (−24 h) or 2 h (−2 h), then washed twice with phosphate buffered saline (PBS). HIV-1 (BaL env-complemented) virus (50 ng of p24; see legend to Table 1) was added for 2 h, then the cells were washed and incubated for 48 h before measurement of luciferase activity in cell lysates as described previously (10, 11). Alternatively, virus and R/Mα/Mβ were added simultaneously to cells, and at the indicated time points (1 h, 3 h, etc) the cells were washed twice in PBS, resuspended in culture medium and incubated for 48 h prior to luciferase assay. Time 0 represents the positive control, to which no β-chemokines were added. +2 h represents the mixture of virus with cells for 2 h prior to washing twice in PBS, addition of R/Mα/Mβ and continuation of the culture for a further 48 h before luciferase assay.

(b) PM1 cells (1×10$^6$) were infected with HIV-1 (500 pg p24) grown in CEM cells (NL4/3; lanes 1-4) or macrophages (ADA; lanes 5-8), in the presence of 500 ng/ml of RANTES (lanes 1 and 5) or MIP-19 (lanes 2 and 6), or with no β-chemokine (lanes 4 and 8). Lanes 3 and 7 are negative controls (no virus). All viral stocks used for the PCR assay were treated with DNAse for 30 min at 37° C., and tested for DNA contamination before use. After 2 h, the cells were washed and resuspended in medium containing the same β-chemokines for a further 8 h. DNA was then extracted from infected cells using a DNA/RNA isolation kit (US Biochemicals). First round nested PCR was performed with primers: U3+, 5'-CAAGGCTACTTCCCTGATTGGCAGAAC-TACACACCAGG-3' (SEQ ID NO:1) preGag, 5'-AGCAAGCCGAGTCCTGCGTCGAGAG-3' (SEQ ID NO:2) and the second round with primers: LTR-test, 5'-GGGACTTTCCGCTGGGGACTTTC 3' (SEQ ID NO:3) LRC2, 5'-CCTGTTCGGGCGCCACTGCTA-GAGATTTTCCAC 3' (SEQ ID NO:4) in a Perkin Elmer 2400 cycler with the following amplification cycles: 94° C. for 5 min, 35 cycles of 94° C. for 30 s, 55° C. for 30 s, 72° C. for 30 s, 72° C. for 7 min. M indicates 1 kb DNA ladder; 1, 10, 100, 1000 indicate number of reference plasmid (pAD8) copies. The assay can detect 100 copies of reverse transcripts.

Figure 4:
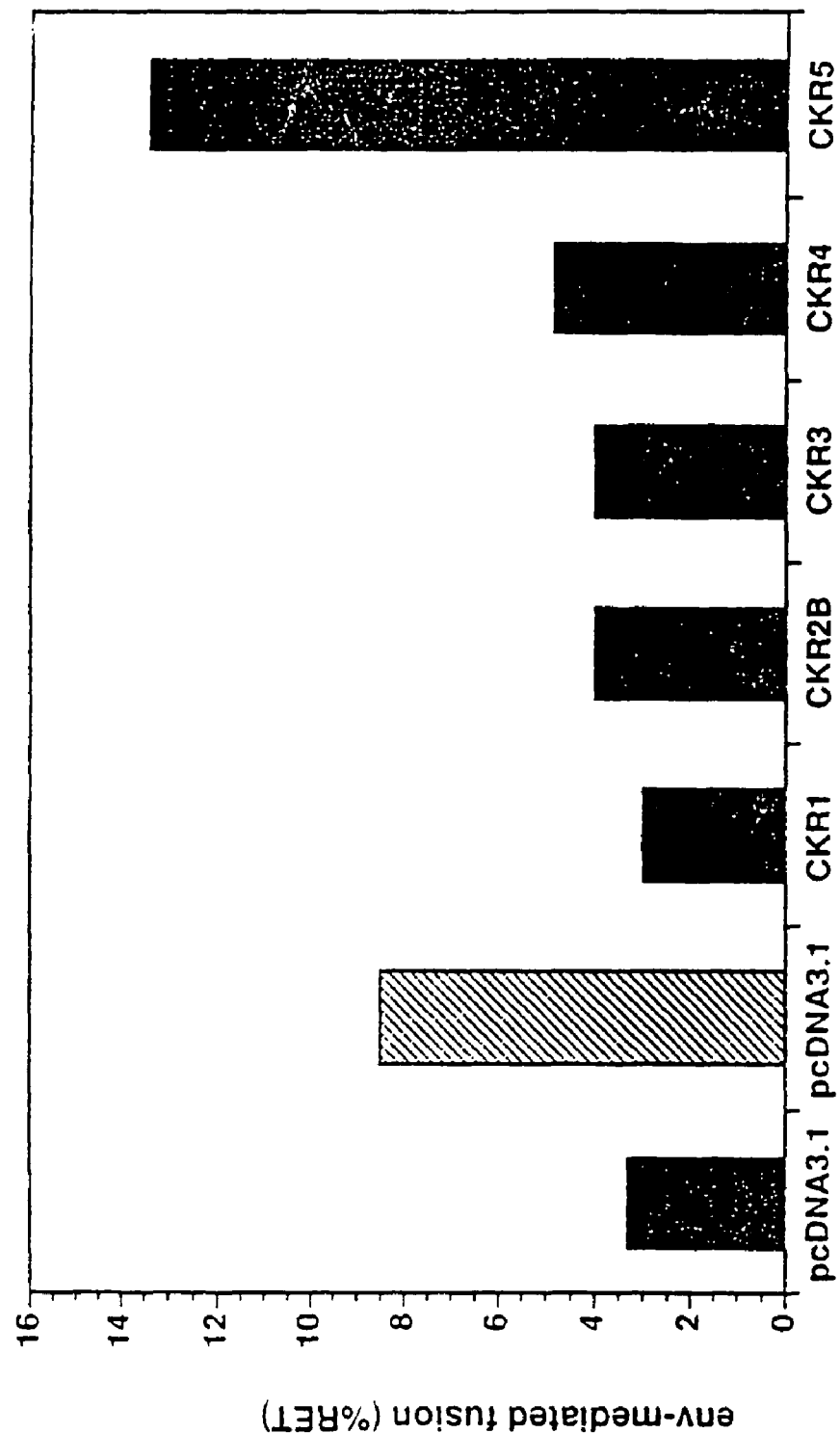

FIG. 4: HIV-1 env-mediated membrane fusion of cells transiently expressing C-C CKR-5.

Membrane fusion mediated by β-chemokine receptors expressed in HeLa cells was demonstrated as follows: Cells were transfected with control plasmid pcDNA3.1 or plasmid pcDNA3.1-CKR constructs using lipofectin (Gibco BRL). The pcDNA3.1 plasmid carries a T7-polymerase promoter and transient expression of β-chemokine receptors was boosted by infecting cells with 1×10$^7$ pfu of vaccinia encoding the T7-polymerase (vFT7.3) 4 h post-lipofection (9). Cells were then cultured overnight in R18-containing media and were tested for their ability to fuse with HeLa-JR-FL cells (filled columns) or HeLa-BRU cells (hatched column) in the RET assay. The % RET with control HeLa cells was between 3% and 4% irrespective of the transfected plasmid.

Figure 5:
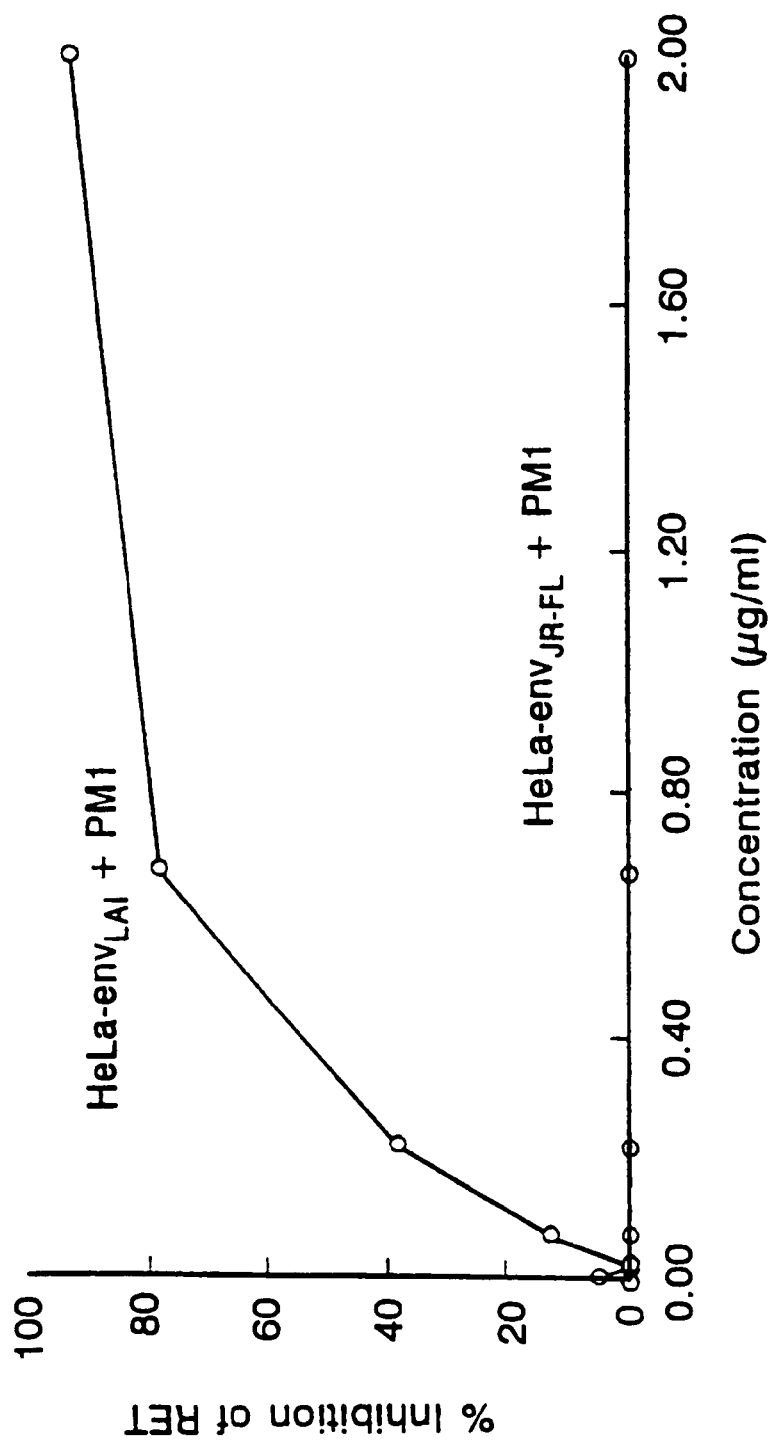

FIG. 5 Membrane fusion mediated by the $HIV_{LAI}$ envelope glycoprotein is inhibited by SDF-1.

% RET resulting from the fusion of PM1 cells and HeLa-$env_{JR-FL}$ or HeLa-$env_{LAI}$ cells (as indicated on the graph) was measured in the presence of recombinant SDF-1α (Gryphon Science, San Francisco) at the indicated concentrations. Experimental method as described in the legend to FIG. 1.

Figure 6A:
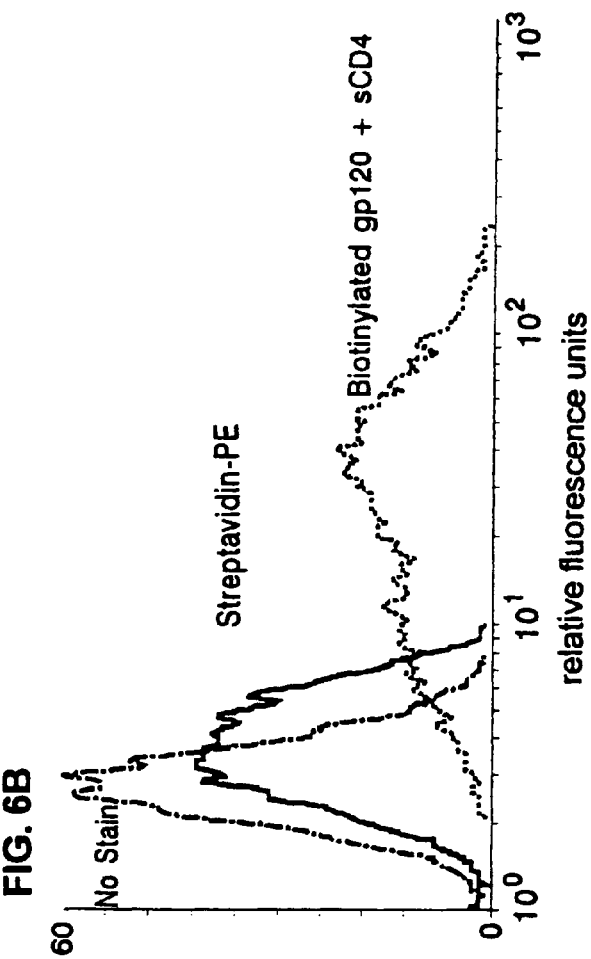
Figure 6B:
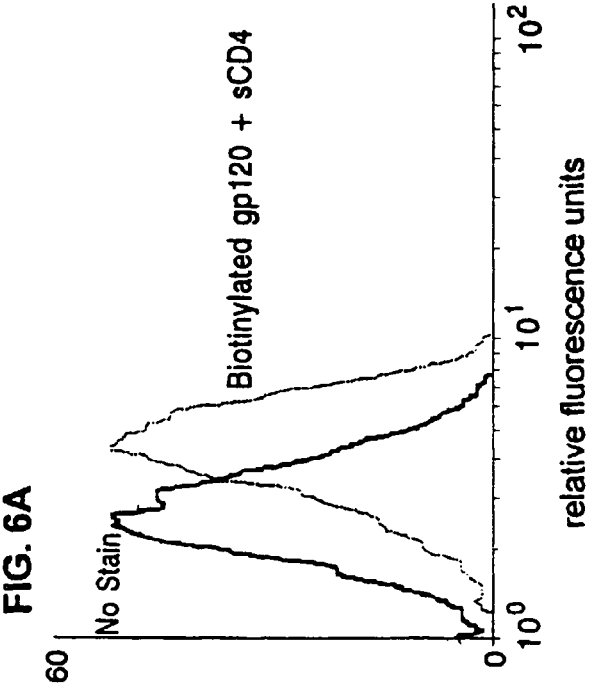

FIG. 6. Flow cytometric analysis of the binding of sCD4-gp120 complexes to (a) CCR5⁻ and (b) CCR5 L1.2 cells, a murine pre-B lymphoma line.

Cells are incubated for 15 min. with equimolar (~100 nM) mixtures of sCD4 and biotinylated HIV-1$_{JR-FL}$ gp120 and then stained with a streptavidin-phycoerythrin conjugate, fixed with 2% paraformaldehyde, and analyzed by FACS. Cell number is plotted on the y-axis.

Figure 7:
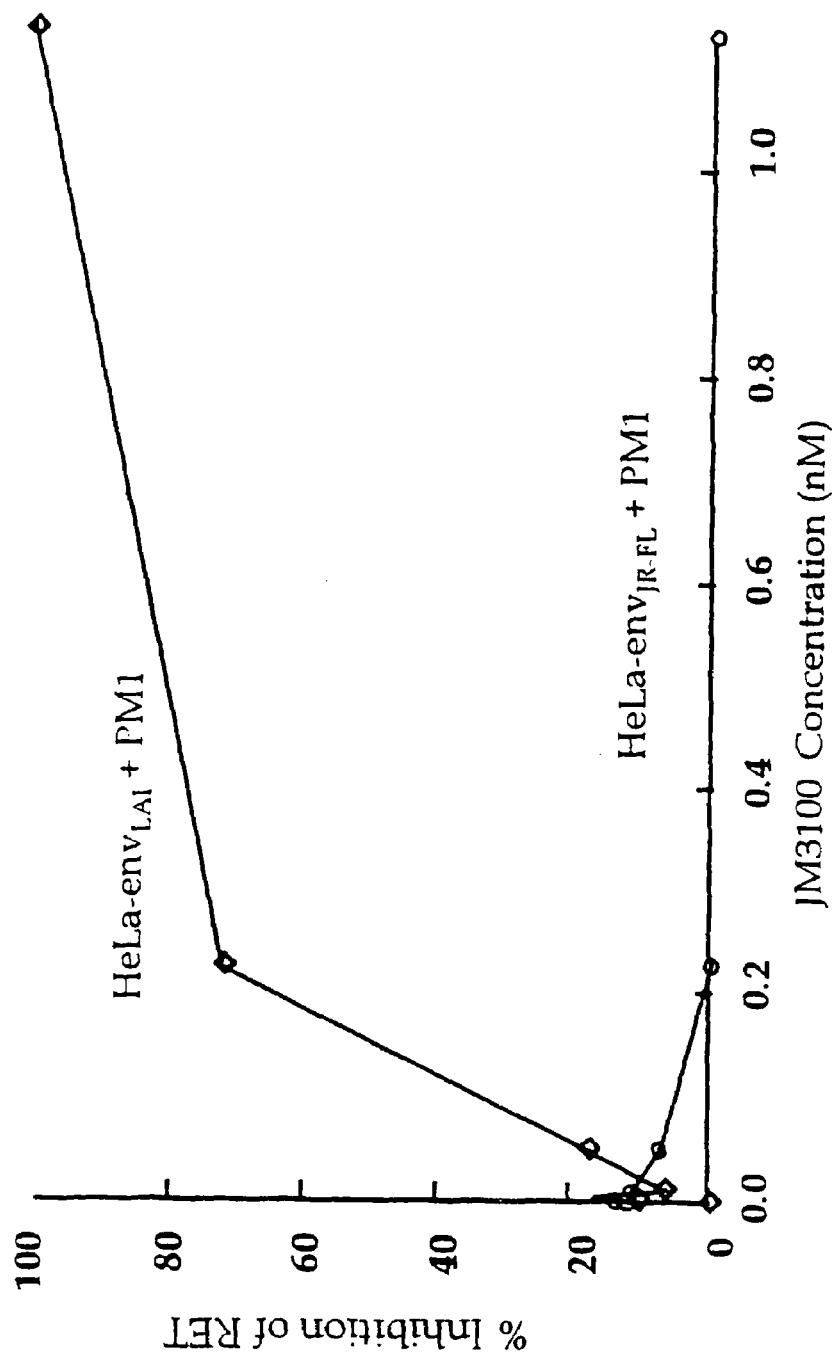

FIG. 7. Inhibition of HIV-1 envelope-mediated cell fusion by the bicyclam JM3100, measured using the RET assay, with the cell combinations indicated.

Figure 8:
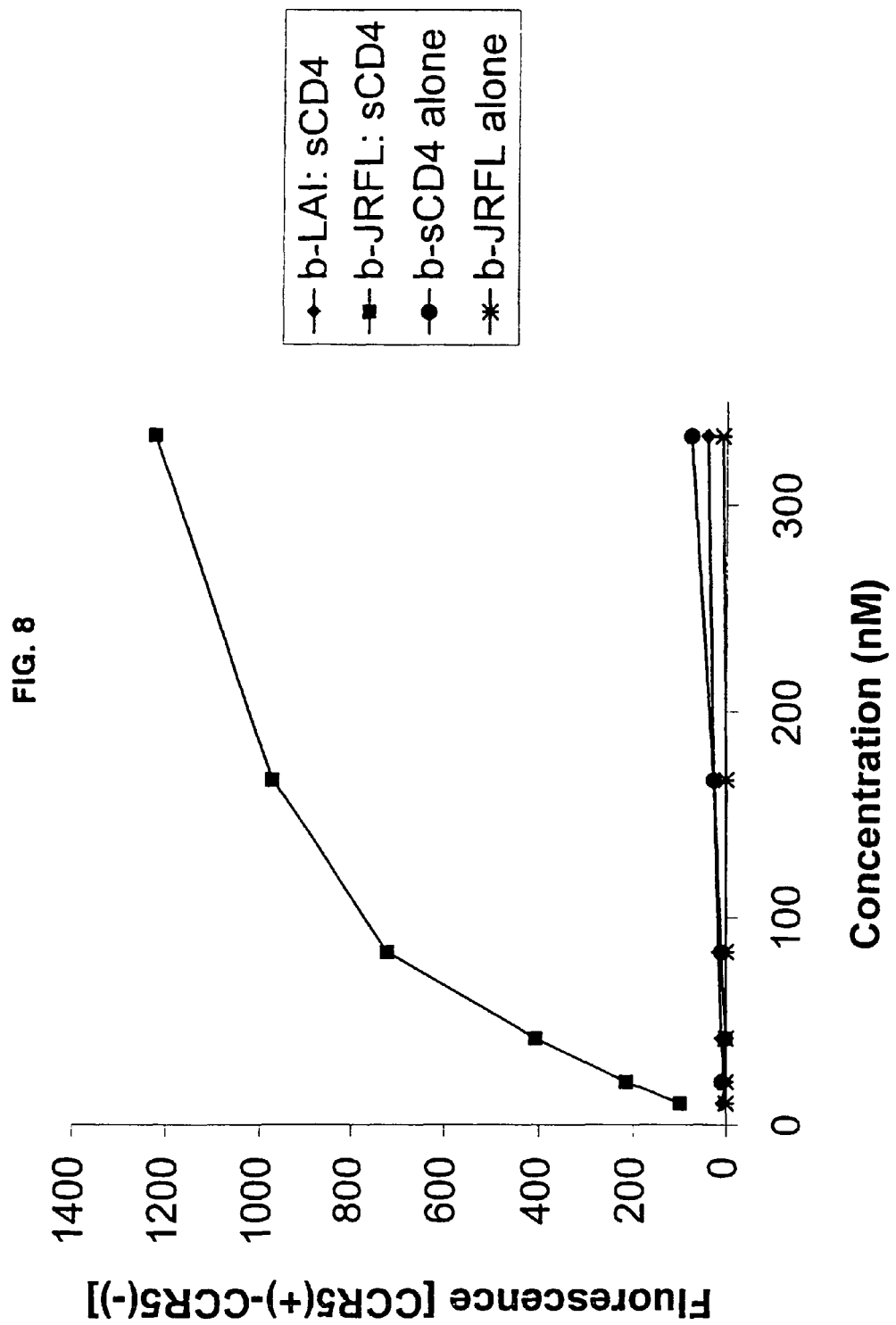

FIG. 8. Binding of CD4 and gp120 to CCR5.

Recombinant soluble CD4 (sCD4) and recombinant gp120 were added in a range of concentrations either individually or as an equimolar molecular complex to recombinant L1.2 cells that express human CCR5 on their cell surface. The recombinant proteins were biotinylated as indicated. Binding was detected by adding a streptavidin-phycoerythrin conjugate and measuring the fluoroescence emission at 590 nm following excitation at 530 nm. The following species were tested:

b-LAI:sCD4: complex formed between scD4 and biotinylated HIV-1$_{LAI}$ gp120 b-JR-FL:sCD4: complex formed between sCD4 and biotinylated HIV-1$_{JR-FL}$ gp120 b-sCD4 alone: biotinylated sCD4 added in the absence of gp120 b-JR-FL alone: biotinylated HIV-1$_{JR-FL}$ gp120 added in the absence of sCD4

These data demonstrate that complexation of soluble CD4 and gp120 is necessary for CCR5 binding, as minimal binding is observed for sCD4 or gp120 alone. The data further demonstrate that binding is observed for sCD4-gp120 complexes when the gp120 is derived from macrophage-tropic (e.g., JR-FL) but not T cell-tropic (e.g., LAI) strains of HIV, as expected from the known relationship between HIV-1 tropism and co-receptor usage. All data have been corrected for residual background binding to nontransfected CCR5-L1.2 cells. To enhance chemokine receptor expression, both transfected and parental L1.2 cells were treated with sodium butyrate prior to assay (Wu et al., J. Exp. Med. 185:1681)

Figure 9:
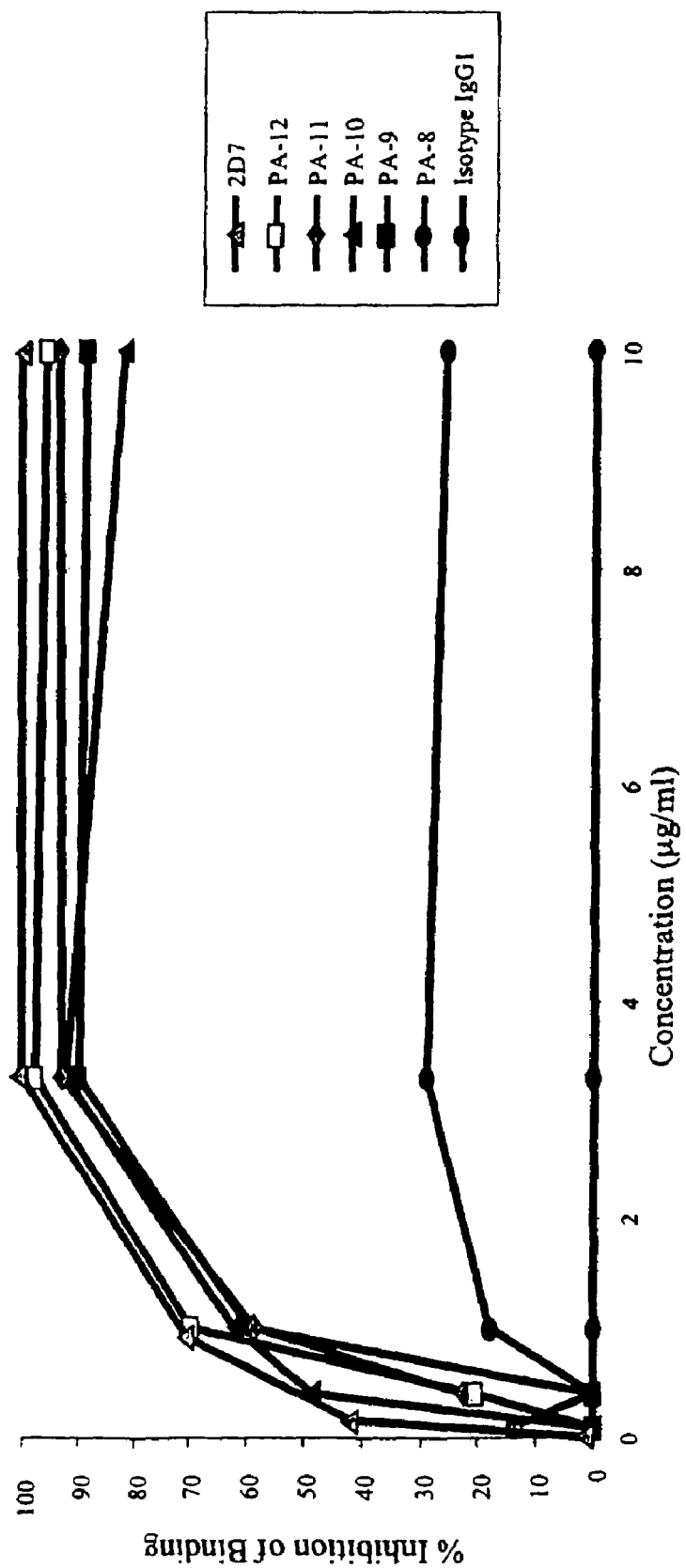

FIG. 9. The CCR5 Binding assay identifies and determines the potency of inhibitors of the gp120-CCR5 interaction.

HIV-1 Inhibitory monoclonal antibodies were added in a range of concentrations to recombinant L1.2 cells that express human CCR5 on their cell surface and used to compete the binding of a complex formed between sCD4 and biotinylated HIV-1$_{JR-FL}$ gp120, whose binding was detected using a streptavidin-phycoerythrin conjugate. PA-8, -9, -10, -11 and -12 are Progenics' monoclonal antibodies that inhibit HIV-1 entry, while 2D7 is a commercially available (Pharmingen, San Diego, Calif.) ant-CCR5 monoclonal antibody that inhibits HIV-1 entry. To enhance chemokine receptor expression, both transfected and parental L1.2 cells were treated with sodium butyrate prior to assay (Wu et al., J. Exp. Med. 185:1681).

DETAILED DESCRIPTION OF THE INVENTION

This invention provides a method for inhibiting fusion of HIV-1 to CD4⁺ cells which comprises contacting CD⁺4 cells with a non-chemokine agent capable of binding to a chemokine receptor in an amount and under conditions such that fusion of HIV-1 to the CD4⁺ cells is inhibited.

This invention also provides a method for inhibiting HIV-1 infection of CD4⁺ cells which comprises contacting CD4⁺ cells with a non-chemokine agent capable of binding to a chemokine receptor in an amount and under conditions such that fusion of HIV-1 to the CD4⁺ cells is inhibited, thereby inhibiting the HIV-1 infection.

In this invention, a chemokine means RANTES, MIP-1-α, MIP-1-β or another chemokine which blocks HIV-1 infection. A chemokine receptor means a receptor capable of binding RANTES, MIP-1-α, MIP-1-β or another chemokine which blocks HIV-1 infection. Such chemokine receptor includes but not limited to CCR5, CXCR4, CCR3 and CCR-2b.

Throughout this application, the receptor "fusin" is also named CXCR4 and the chemokine receptor C-C CKR5 is also named CCR5.

The HIV-1 used in this application unless specified will mean clinical or primary or field isolates or HIV-1 viruses which maintain their clinical characteristics. The HIV-1 clinical isolates may be passaged in primary peripheral blood mononuclear cells. The HIV-1 clinical isolates may be macrophage-trophic.

The non-chemokine agents of this invention are capable of binding to chemokine receptors and inhibiting fusion of HIV-1 to CD4⁺ cells. The non-chemokine agents include, but are not limited to, chemokine fragments and chemokine derivatives and analogues, but do not include naturally occurring chemokines. The non-chemokine agents include multimeric forms of the chemokine fragments and chemokine derivatives and analogues or fusion molecules which contain chemokine fragments, derivatives and analogues linked to other molecules.

The non-chemokine agents do not include bicyclams and their derivatives as described in U.S. Pat. No. 5,021,409, issued Jun. 4, 1991, the content of which is incorporated by reference into this application. Some bicyclam derivatives have been previously described with antiviral activities (15, 16).

In an embodiment of this invention, the non-chemokine agent is an oligopeptide. In another embodiment, the non-chemokine agent is a polypeptide. In still another embodiment, the non-chemokine agent is an antibody or a portion thereof. Antibodies against the chemokine receptor may easily be generated by routine experiments. It is also within the level of ordinary skill to synthesize fragments of the antibody capable of binding to the chemokine receptor. In a further embodiment, the non-chemokine agent is a nonpeptidyl agent.

Non-chemokine agents which are purely peptidyl in composition can be either chemically synthesized by solid-phase methods (Merrifield, 1966) or produced using recombinant technology in either prokaryotic or eukaryotic systems. The synthetic and recombinant methods are well known in the art.

Non-chemokine agents which contain biotin or other non-peptidyl groups can be prepared by chemical modification of synthetic or recombinant chemokines or non-chemokine agents. One chemical modification method involves periodate oxidation of the 2-amino alcohol present on chemokines or non-chemokine agents possessing serine or threonine as their N-terminal amino acid (Geophegan and Stroh, 1992). The resulting aldehyde group can be used to link peptidyl or non-peptidyl groups to the oxidized chemokine or non-chemokine agent by reductive amination, hydrazine, or other chemistries well known to those skilled in the art.

As used herein, a N-terminus of a protein should mean the terminus of the protein after it has been processed. In case of a secretory protein which contains a cleavable signal sequence, the N-terminus of a secretory protein should be the terminus after the cleavage of a signal peptide.

This invention provides a method of identifying these non-chemokine agents. One way of identifying such agents, including non-peptidyl agents, that bind to a chemokine receptor and inhibit fusion of HIV-1 to CD4+ cells is to use the following assay: 1) Incubate soluble CD4 with biotinylated gp120 from HIV-1$_{JR-FL}$ or HIV-1$_{LAI}$; 2) Incubate this complex with CCR5 or CXCR4-expressing cells (for HIV-1$_{JR-FL}$ or HIV-1$_{LAI}$ gp120s, respectively) that do not express CD4, in the presence of absence of a candidate inhibitor; 3) Wash and then incubate with streptavidin-phycoerythrin; and 4) Wash and then measure the amount of bound gp120 using a flow cytometer or fluorometer and calculate the degree of inhibition of binding by the inhibitor.

Alternative methods to detect bound gp120 can also be used in place of the biotinylated gp120-streptavidin-phycoerythrin method described above. For example, peroxidase-conjugated gp120 could be used in place of the biotinylated gp120 and binding detected using an appropriate calorimetric substrate for peroxidase, with a spectrometric readout.

This invention further provides the non-chemokine agents identified by the above methods.

This invention provides a non-chemokine agent capable of binding to the chemokine receptor and inhibiting fusion of HIV-1 to CD4+ cells with the proviso that the agent is not a known bicyclam or its known derivatives. In an embodiment, the non-chemokine is a polypeptide. In a further embodiment, this polypeptide is a fragment of the chemokine RANTES (Gong et al., 1996). In a still further embodiment, the polypeptide may also comprise the RANTES sequence with deletion of the N-terminal amino acids of said sequence. The deletion may be the first eight N-terminal amino acids of the RANTES sequence (SEQ ID NO:5).

In a separate embodiment, the polypeptide may comprise the MIP-1β sequence with deletion of the N-terminal amino acids of said sequence. The deletion may be the first seven, eight, nine or ten N-terminal amino acids of the MIP-1β sequence.

In another embodiment of non-chemokine agent, the polypeptide comprises the MIP-1β sequence with the N-terminal sequence modified by addition of an amino acid or oligopeptide. In a separate embodiment, the polypeptide comprises the MIP-1β sequence with the N-terminal sequence modified by removing the N-terminal alanine and replaced it by serine or threonine and additional amino acid or oligopeptide or nonpeptidyl moiety. In a further embodiment, the additional amino acid is methionine.

As described infra in the section of Experimental Details, a cofactor for HIV-1 fusion and entry was identified and designated "fusin" (Feng et al., 1996). This invention provides an agent which is capable of binding to fusin and inhibiting infection. In an embodiment, the agent is an oligopeptide. In another embodiment, the agent is an polypeptide.

In a further embodiment, the polypeptide comprises SDF-1 with deletion of the N-terminal amino acids of said sequence. The deletion may be the first six, seven, eight, or nine N-terminal amino acids of the SDF-1 sequence.

This invention also provides the above non-chemokine agent, wherein the polypeptide comprises SDF-1 sequence with the N-terminal sequence modified to produce antagonistic effect to SDF-1. One modification is to replace the N-terminal glycine of SDF-1 by serine and derivatized with biotin. Another modification is to replace the N-terminal glycine of SDF-1 by serine and derivatized with methionine. A further modification is to add the N-terminus of SDF-1 with a methionine before the terminal glycine.

In still another embodiment, the agent is an antibody or a portion of an antibody. In a separate embodiment, the agent is a nonpeptidyl agent.

The agents capable of binding to fusin may be identified by screening different compounds for their capability to bind to fusin in vitro.

A suitable method has been described by Fowlkes, et al. (1994), international application number: PCT/US94/03143, international publication number: WO 94/23025, the content of which is incorporated by reference into this application. Briefly, yeast cells having a pheromone system are engineered to express a heterologous surrogate of a yeast pheromone system protein. The surrogate incorporates fusin and under some conditions performs in the pheromone system of the yeast cell a function naturally performed by the corresponding yeast pheromone system protein. Such yeast cells are also engineered to express a library of peptides whereby a yeast cell containing a peptide which binds fusin exhibits modulation of the interaction of surrogate yeast pheromone system protein with the yeast pheromone system and this modulation is a selectable or screenable event. Similar approaches may be used to identify agents capable of binding to both fusin and the chemokine receptor C-C CKR-5.

This invention also provides pharmaceutical compositions comprising an amount of such non-chemokine agents or agents capable of binding to fusin effective to inhibit fusion of HIV-1 to CD4+ cells and a pharmaceutically acceptable carrier.

Pharmaceutically acceptable carriers are well known to those skilled in the art. Such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

This invention provides a composition of matter capable of binding to the chemokine receptor and inhibiting fusion of HIV-1 to CD4+ cells comprising a non-chemokine agent linked to a ligand capable of binding to a cell surface receptor of the CD4+ cells other than the chemokine receptor such that the binding of the non-chemokine agent to the chemokine receptor does not prevent the binding of the ligand to the other receptor. In an embodiment, the cell surface receptor is CD4. In another embodiment, the ligand is an antibody or a portion of an antibody.

This invention also provides a pharmaceutical composition comprising an amount of an above-described composition of matter effective to inhibit fusion of HIV-1 to CD4+ cells and a pharmaceutically acceptable carrier.

This invention provides a composition of matter capable of binding to the chemokine receptor and inhibiting fusion of HIV-1 to CD4+ cells comprising a non-chemokine agent linked to a compound capable of increasing the in vivo half-life of the non-chemokine agent. In an embodiment, the compound is polyethylene glycol.

This invention also provides a pharmaceutical composition comprising an amount of a composition of matter comprising a non-chemokine agent linked to a compound capable of increasing the in vivo half-life of the non-chemokine agent effective to inhibit fusion of HIV-1 to CD4+ cells and a pharmaceutically acceptable carrier.

This invention provide methods for reducing likelihood of HIV-1 infection in a subject comprising administering the above-described pharmaceutical compositions to the subject. This invention also provides methods for treating HIV-1 infection in a subject comprising administering the above-described pharmaceutical compositions to the subject.

This invention also provides methods for determining whether a non-chemokine agent is capable of inhibiting the fusion of HIV-1 to a CD4+ cell which comprise: (a) contacting (i) a CD4+ cell which is labeled with a first dye and (ii) a cell expressing the HIV-1 envelope glycoprotein on its surface which is labeled with a second dye, in the presence of an excess of the agent under conditions permitting the fusion of the CD4+ cell to the cell expressing the HIV-1 envelope glycoprotein on its surface in the absence of the agent, the first and second dyes being selected so as to allow resonance energy transfer between the dyes; (b) exposing the product of step (a) to conditions which would result in resonance energy transfer if fusion has occurred; and (c) determining whether there is a reduction of resonance energy transfer, when compared with the resonance energy transfer in the absence of the agent, a decrease in transfer indicating that the agent is capable of inhibiting fusion of HIV-1 to CD4+ cells.

HIV-1 only fuses with appropriate CD4+ cells. For example, laboratory-adapted T lymphotropic HIV-1 strains fuse with most CD4+ human cells. Clinical HIV-1 isolates do not fuse with most transformed CD4+ human cell lines but do fuse with human primary CD4+ cells such as CD+4 T lymphocytes and macrophages. Routine experiments may be easily performed to determine whether the CD4+ cell is appropriate for the above fusion assay.

As described in this invention, HIV-1 membrane fusion is monitored by a resonance energy transfer assay. The assay was described in the International Application Number, PCT/US94/14561, filed Dec. 16, 1994 with International Publication Number WO 95/16789. This assay is further elaborated in a U.S. co-pending application Ser. No. 08/475,515, filed Jun. 7, 1995. The contents of these applications are hereby incorporated by reference into this application.

In an embodiment of the above method, the non-chemokine agent is an oligopeptide. In another embodiment, the non-chemokine agent is a polypeptide. In still another embodiment, the agent is an antibody or a portion thereof. In a further embodiment, the non-chemokine agent is a nonpeptidyl agent.

In a separate embodiment, the CD4+ cell is a PM1 cell. In another embodiment, the cell expressing the HIV-1 envelope glycoprotein is a HeLa cell expressing HIV-1$_{JR-FL}$ gp120/gp41.

This invention provides a method for determining whether an agent is capable of inhibiting HIV-1 infection comprising steps of: (a) contacting an appropriate concentration of an agent with a chemokine receptor or a portion thereof under conditions permitting the binding of the agent to the chemokine receptor; (b) contacting the chemokine receptor resulting from step (a) with a gp120/CD4 complex under conditions permitting the binding of the gp120/CD4 complex and the chemokine receptor in the absence of the agent; (c) measuring the amount of bound gp120/CD4 complex wherein a decrease in the amount compared with the amount determined in the absence of the agent indicates that the agent is capable of inhibiting HIV-1 infection.

As used herein, the portion of the chemokine receptor used in the above method is the portion which maintains the capability of binding to HIV, i.e. capable of interaction with the gp120/CD4 complex. It is the intention of this invention to cover hybrid molecules or genetically engineered molecules which comprise this portion or domain of the chemokine receptor.

The gp120/CD4 complex used in the assay may include a truncated form of either molecules or hybrid proteins of molecules as long as the domain for binding to the chemokine receptor is retained.

This invention provides a method for determining whether an agent is capable of inhibiting HIV-1 infection comprising steps of: (a) fixing a chemokine receptor on a solid matrix; (b) contacting the agent with the fixed chemokine receptor under conditions permitting the binding of the agent to the chemokine receptor; (c) removing the unbound agent; (d) contacting the fixed chemokine receptor resulting in step (c) with a gp120 in the presence of CD4 under conditions permitting the binding of the gp120/CD4 complex and the chemokine receptor in the absence of the agent; (e) measuring the amount of bound gp120/CD4 complex; and (f) comparing the amount determined in step (d) with the amount determined in the absence of the agent, a decrease of the amount indicating that the agent is capable of inhibiting HIV-1 infection.

This invention also provides a method for determining whether an agent is capable of inhibiting HIV-1 infection comprising steps of: (a) fixing a chemokine receptor on a solid matrix; (b) contacting the agent with the fixed chemokine receptor; (c) contacting the mixture in step (b) with a gp120 in the presence of CD4 under conditions permitting the binding of the gp120/CD4 complex and the chemokine receptor in the absence of the agent; (d) measuring the amount of bound gp120/CD4 complex; and (e) comparing the amount determined in step (d) with the amount determined in the absence of the agent, a decrease of the amount indicating that the agent is capable of inhibiting HIV-1 infection.

This invention also provides a method for determining whether an agent is capable of inhibiting HIV-1 infection comprising steps of: (a) contacting the agent with a gp120/CD4 complex under conditions permitting the binding of the agent to the gp120/CD4 complex; (b) contacting the gp120/CD4 complex resulting from step (a) with a chemokine receptor under conditions permitting the binding of the gp120/CD4 complex and the chemokine receptor in the absence of the agent; (c) measuring the amount of bound chemokine receptor, wherein a decrease of the amount when compared with the amount determined in the absence of the agent indicates that the agent is capable of inhibiting HIV-1 infection.

This invention also provides a method for determining whether an agent is capable of inhibiting HIV-1 infection comprising steps of: (a) fixing a gp120/CD4 complex on a solid matrix; (b) contacting the agent with the fixed gp120/CD4 complex under conditions permitting the binding of the agent to the gp120/CD4 complex; (c) removing unbound agent; (d) contacting the fixed gp120/CD4 complex resulting from step (c) with a chemokine receptor under conditions permitting the binding of the gp120/CD4 complex and the chemokine receptor in the absence of the agent; (e) measuring the amount of bound chemokine receptor; and (f) comparing the amount determined in step (e) with the amount determined in the absence of the agent, a decrease of the amount indicating that the agent is capable of inhibiting HIV-1 infection.

This invention provides a method for determining whether an agent is capable of inhibiting HIV-1 infection comprising steps of: (a) fixing a gp120/CD4 on a solid matrix; (b) contacting the agent with the fixed gp120/CD4 complex; (c) contacting the mixture in step (b) with a chemokine receptor under conditions permitting the binding of the gp120/CD4 complex and the chemokine receptor in the absence of the agent; (d) measuring the amount of bound chemokine receptor; (e) comparing the amount determined in step (d) with the amount determined in the absence of the agent, a decrease of the amount indicating that the agent is capable of inhibiting HIV-1 infection.

As used in these assays, CD4 include soluble CD4, fragments of CD4 or polypeptides incorporating the gp120 binding site of CD4 capable of binding gp120 and enabling the binding of gp120 to the appropriate chemokine receptor.

As used in these assay gp120 is the gp120 from an appropriate strain of HIV-1. For example, gp120 from the macrophage tropic clinical isolate HIV-$1_{JR-FL}$ will bind to the chemokine receptor CCR5, whereas gp120 from the laboratory adapted T-tropic strain HIV-$1_{LAI}$ will bind to the chemokine receptor CXCR4.

In a preferred embodiment of the above methods, the CD4 is a soluble CD4. The chemokine receptor which may be used in the above assay includes CCR5, CXCR4, CCR3 and CCR-2b.

In an embodiment, the chemokine receptor is expressed on a cell. In another embodiment, the chemokine receptor is embedded in liposomes. In further embodiment, the chemokine receptor is embedded in a membrane derived from cells expressing the chemokine receptor. In a preferred embodiment, the cell is a L1.2 cell. In a separate embodiment, the chemokine receptor is purified and reconstituted in liposomes. Such chemokine receptor embedded in the lipid bilayer of liposomes retains the gp120 binding activity of the receptor.

The gp120, CD4 or both may be labelled with a detectable marker in the above assays. Markers including radioisotope or enzymes such as horse radish peroxidase may be used in this invention.

In an embodiment, the gp120 or CD4 or the chemokine receptor is labelled with biotin. In a further embodiment, the biotinylated gp120, or CD4 or the chemokine receptor is detected by: (i) incubating with streptavidin-phycoerythrin, (ii) washing the incubated mixture resulting from step (i), and (iii) measuring the amount of bound gp120 using a plate reader, exciting at 530 nm, reading emission at 590 nm.

This invention also provides an agent determined to be capable of inhibiting HIV-1 infection by the above methods, which is previously unknown.

This invention also provides a pharmaceutical composition comprising the agent determined to be capable of inhibiting HIV-1 infection by the above methods and a pharmaceutically acceptable carrier. In an embodiment, the agent is an oligopeptide. In another embodiment, the agent is a polypeptide. In a still another embodiment, the agent is a nonpeptidyl agent.

This invention also provides a molecule capable of binding to the chemokine receptor CCR5 and inhibiting fusion of HIV-1 to CD4$^+$ cells comprising the above determined agent linked to a compound capable of increasing the in vivo half-life of the non-chemokine agent. In an embodiment, the compound is polyethylene glycol. This invention also provides a pharmaceutical composition comprising an amount of the above molecule effective to inhibit HIV-1 infection and a pharmaceutically acceptable carrier.

This invention provides a method for reducing the likelihood of HIV-1 infection in a subject comprising administering the above pharmaceutical compositions to the subject.

This invention provides a method for treating HIV-1 infection in a subject comprising administering the above pharmaceutical composition to the subject.

This invention will be better understood by reference to the Experimental Details which follow, but those skilled in the art will readily appreciate that the specific experiments detailed are only illustrative of the invention as described more fully in the claims which follow thereafter.

Experimental Details

First Series of Experiments

1) Chemokines Inhibit Fusion Mediated by the Envelope Glycoprotein from a Macrophage-Tropic Primary Isolate of HIV-1 but not from a Laboratory-Adapted T-Lymphotrophic Strain of the Virus The chemokines RANTES, MIP-1α and MIP-1β were obtained from R & D systems (Minneapolis, Minn.). They were tested in the RET assay for ability to inhibit fusion between HeLa-env$_{JR-FL}$ cells (expressing gp120/gp41 from the macrophage tropic isolate HIV-$1_{JR-FL}$) and PM1 cells, or for inhibition of fusion between HeLa-env$_{LAI}$ cells (expressing gp120/gp41 from the laboratory-adapted strain HIV-$1_{LAI}$) and various CD4$^+$ T lymphocyte cell lines. As shown in FIG. 1, all three chemokines inhibited fusion mediated by the macrophage tropic virus envelope glycoprotein, but not that mediated by the laboratory-adapted strain envelope glycoprotein.

The ability of the chemokines to block the interaction between CD4 and HIV-1 gp120 which occurs at virus attachment was then tested. It was found that the chemokines did not inhibit this interaction (FIG. 2), demonstrating that their blockade of HIV-1 envelope glycoprotein-mediated membrane fusion occurs at the membrane fusion event itself, rather than the initial CD4-gp120 interaction which precedes fusion.

2) Non-Chemokine Peptides and Derivatives that Inhibit HIV-1 Fusion

The non-chemokines include chemokine fragments and chemokine derivatives that are tested in the RET assay to determine which are active in inhibiting HIV-1 membrane fusion. Particular attention is focused on fragments or derivatives that inhibit HIV-1 fusion but do not activate leukocyte responses. These non-chemokines include:

a) N-terminal derivatives of the chemokines. Addition of residues to the N-terminus of chemokines inhibits the function of these proteins without significantly reducing their ability to bind chemokine receptors. For example, Met-RANTES (RANTES with an N-terminal methionine) has been shown to be a powerful antagonist of native RANTES and is unable to induce chemotaxis or calcium mobilization in certain systems. The mechanism of antagonism appears to be competition for receptor binding (9). Similar results were found using other derivatives of the N terminus of RANTES (9) and also by N-terminal modification of other chemokines, such as IL-8 (a member of the C-X-C chemokines) (10). The current invention includes Met-RANTES and other chemokines derivatised by the addition of methionine, or other residues, to the N-terminus so that they inhibit fusion mediated by the envelope glycoprotein of HIV-1$_{JR-FL}$, and inhibit infection by many isolates of HIV-1, yet do not activate the inflammatory response.

b) Chemokines with N-terminal amino acids deleted: Chemokine antagonists have been generated by deleting amino acids in the N-terminal region. For example, deletion of up to 8 amino acids at the N-terminus of the chemokine MCP-1 (a member of the C-C chemokine group), ablated the bioactivity of the protein while allowing it to retain chemokine receptor binding and the ability to inhibit activity of native MCP-1 (11, 12).

The current invention includes N-terminal deletants of RANTES, MIP-1α and MIP-1β, lacking the biological activity of the native proteins, which inhibit HIV-1 fusion and HIV-1 infection.

c) Other peptides: A series of overlapping peptides (e.g. of 20-67 residues) from all regions of RANTES, MIP-1α and MIP-1β are screened by the same approaches to identify peptides which inhibit HIV-1 fusion most potently without activating leukocytes. Activation of leukocyte responses is measured following routine procedures (9, 10, 11, 12).

3) Cloning the Chemokine Receptors

Chemokine receptors required for HIV-1 fusion are cloned by the following strategy. First a cDNA library is made in a mammalian expression vector (e.g. pcDNA3.1 from Invitrogen Corp. San Diego, Calif.) using mRNA prepared from the PM1 cell line or $CD4^+$ T-lymphocytes or macrophages. Degenerate oligonucleotide probes are used to identify members of the cDNA library encoding members of the chemokine receptor family, for example following previously published methods (2). The vectors containing chemokine receptor cDNAs are then individually expressed in one of several mammalian cell lines which express human CD4 but do not fuse with HeLa-$env_{JR-FL}$ cells (e.g. HeLa-CD4, CHO-CD4 or COS-CD4) or HeLa-$env_{LAI}$ cells (e.g. CHO-CD4 or COS-CD4). Following analysis in the RET assay, clones which gain the ability to fuse with HeLa-$env_{JR-FL}$ or HeLa-$env_{LAI}$ are identified and the coding sequences recovered, for example by PCR amplification, following procedures well known to those skilled in the art. DNA sequencing is then performed to determine whether the cDNA recovered encodes a known chemokine receptor. Following expression of the receptor, monoclonal and polyclonal antibodies are prepared and tested for ability to inhibit infection by a panel of HIV-1 isolates.

REFERENCES OF THE FIRST SERIES OF EXPERIMENTS

1. Cocchi, F., DeVico, A. L., Garzino-Demo, A., Arya, S. K., Gallo, R. C., Lusso, P. 1995. *Science.* 270:1811-1815.
2. Raport, C. J., Schweickart, V. L., Chantry, D., Eddy Jr., R. L., Shows, T. B., Godiska, R., Gray, P. W. 1996. *Journal of Leukocyte Biology.* 59: 18-23.
3. Maddon P J., Dalgleish A G., McDougal J S., Clapham P R., Weiss R A., Axel R. 1986. *Cell.* 47:333-348.
4. Ashorn P A., Berger E A., Moss B. 1990. *J. Virol.* 64:2149-2156.
5. Clapham P R., Blanc D., Weiss R A. 1991. *Virology.* 181: 703-715.
6. Harrington R D., Geballe A P. 1993. *J. Virol.* 67:5939-5947.
7. Broder C C., Dimitrov D S., Blumenthal R., Berger E A. 1993. *Virology.* 193:483-491.
8. Dragic T., Charneau P., Clavel F., Alizon M. 1992. *J. Virol.* 66:4794-4802.
9. Wells, T. N., Power, C. A., Lusti-Narasimhan, M., Hoogewerf, A. J., Cooke, R. M., Chung, C. W., Peitsch, M. C., Proudfoot, A. E. 1996. *Journal of Leukocyte Biology.* 59:53-60.
10. Moser, B., Dewald, B., Barella, L., Schumacher, C., Baggiolini, M., Clark-Lewis, I. 1993. *Journal of Biological Chemistry.* 268:7125-7128.
11. Gong, J. H., Clark-Lewis, I. 1995. *J. Exp. Med.* 181:631-640.
12. Zhang, Y. J., Rutledge, B. J., Rollins, B. J. 1994. *Journal of Biological Chemistry.* 269:15918-15924.
13. Merrifield, R. B. (1963) *J. Am. Chem. Soc.* 85: 2149-2154.
14. Goeghegan, K. F. Stroh, J. F. (1992) *Bioconjugate Chem.* 3: 138-146.
15. Clercq, E. D. et al. (1994) *Antimicrobial Agents and Chemotherapy* 38:668-674.
16. Clercq, E. D. et al (1992) *Proc. Natl. Acad. Sci. USA* 89: 5286-5290.

Second Series of Experiments

The replication of primary, non-syncytium-inducing (NSI) HIV-1 isolates in $CD4^+$ T-cells is inhibited by the C-C β-chemokines MIP-1α, MIP-1β and RANTES (1, 2), but T-cell line-adapted (TCLA) or syncytium-inducing (SI) primary strains are insensitive (2, 3). The β-chemokines are small (8 kDa), related proteins active on cells of the lymphoid and monocyte lineage (4-8). Their receptors are members of the 7-membrane-spanning, G-protein-linked superfamily, one of which (the LESTR orphan receptor) has been identified as the second receptor for TCLA HIV-1 strains, and is now designated fusin (9). Fusin is not known to be a 9-chemokine receptor (7-9).

To study how β-chemokines inhibit HIV-1 replication, a virus entry assay based on single-cycle infection by an env-deficient virus, NL4/3Δenv (which also carries the luciferase reporter gene), complemented by envelope glycoproteins expressed in trans was used (10, 11). Various env-complemented viruses were tested in PM1 cells, a variant of HUT-78 that has the unique ability to support replication of primary and TCLA HIV-1 strains, allowing comparison of envelope glycoprotein functions against a common cellular background (2, 12). MIP-1α, MIP-1β and RANTES are most active against HIV-1 in combination (2, 3), and strongly inhibited infection of PM1 cells by complemented viruses whose envelopes are derived from the NSI primary strains ADA and BaL (Table 1a).

TABLE 1

Inhibition of HIV-1 entry in PM1 cells and $CD4^+$ T-cells by β-chemokines

| a) | % luciferase activity | | | | |
|---|---|---|---|---|---|
| PM1 cells | BaL | ADA | NL4/3 | HxB2 | MuLV |
| control without virus | 2 | 2 | 2 | 5 | 3 |
| control with virus | 100 | 100 | 100 | 100 | 100 |
| +R/Mα/Mβ (50/50/50) | 2 | 3 | 92 | 117 | 100 |
| +RANTES (100) | 1 | 1 | nd | nd | nd |
| +MIP-1α(100) | 54 | 54 | nd | nd | nd |
| +MIP-1β (100) | 1 | 6 | nd | nd | nd |
| +MCP-1 (100) | 46 | 50 | nd | nd | nd |
| +MCP-2 (100) | 28 | 26 | nd | nd | nd |
| +MCP-3 (100) | 58 | 46 | nd | nd | nd |

TABLE 1-continued

Inhibition of HIV-1 entry in PM1 cells and
CD4+ T-cells by β-chemokines

| b) | JR-FL | HxB2 | MuLV |
|---|---|---|---|
| LW4 CD4+ T-cells | | | |
| control without virus | 1 | 1 | 1 |
| control with virus | 100 | 100 | 100 |
| +R/Mα/Mβ (200/200/200) | 14 | 68 | nd |
| LW5 CD4+ T-cells | | | |
| control without virus | 1 | 1 | 1 |
| control with virus | 100 | 100 | 100 |
| +R/Mα/Mβ (200/200/200) | 15 | 73 | nd |

Table 1 Legend:

PM1 cells were cultured as described by Lusso et al (12). Ficoll/hypaque-isolated PBMC from laboratory workers (LW) stimulated with PHA for 72 h before depletion of CD8+ Lymphocytes with anti-CD8 immunomagnetic beads (DYNAL, Great Neck, N.Y.). CD4+ Lymphocytes were maintained in culture medium containing interleukin-2 (100 U/ml; Hofmann LaRoche, Nutley, N.J.), as described previously (3). Target cells ($1-2\times10^5$) were infected with supernatants (10-50 ng of HIV-1 p24) from 293-cells co-transfected with an NL4/3Δenv-luciferase vector and a HIV-1 env-expressing vector (10, 11). β-Chemokines (R & D Systems, Minneapolis) were added to the target cells simultaneously with virus, at the final concentrations (ng/ml) indicated in parentheses in the first column. The β-chemokine concentration range was selected based on prior studies (2, 3). After 2 h, the cells were washed twice with PBS, resuspended in β-chemokine-containing media and maintained for 48-96 h. Luciferase activity in cell lysates was measured as described previously (10, 11). The values indicated represent luciferase activity (cpm)/ng p24/mg protein, expressed relative to that in virus-control cultures lacking β-chemokines (100%), and are the means of duplicate or sextuplicate determinations. nd, not done. R/Mα/Mβ, RANTES+MIP-1α+MIP-1β.

RANTES and MIP-1β were strongly active when added individually, while other β-chemokines—MIP-1α, MCP-1, MCP-2 and MCP-3 (refs. 13-15)—were weaker inhibitors (Table 1a). However, MIP-1α, MIP-1β and RANTES, in combination, did not inhibit infection of PM1 cells by the TCLA strains NL4/3 and HxB2, or by the amphotropic murine leukemia virus (MuLV-Ampho) pseudotype (Table 1a). Thus, phenotypic characteristics of the HIV-1 envelope glycoproteins influence their sensitivity to β-chemokines in a virus entry assay.

The env-complementation assay was used to assess HIV-1 entry into CD4+ T-cells from two control individuals (LW4 and LW5). MIP-1α, MIP-1β and RANTES strongly inhibited infection by the NSI primary strain JR-FL infection of LW4's and LW5's CD4+ T-cells, and weakly reduced HxB2 infection of UV cells (Table 1b), suggesting that there may be some overlap in receptor usage on activated CD4+ T-cells by different virus strains. BaL env-mediated replication in normal PBL was also inhibited by MIP-1α, MIP-1β and RANTES, albeit with significant inter-donor variation in sensitivity (data not shown).

Figure 3A:
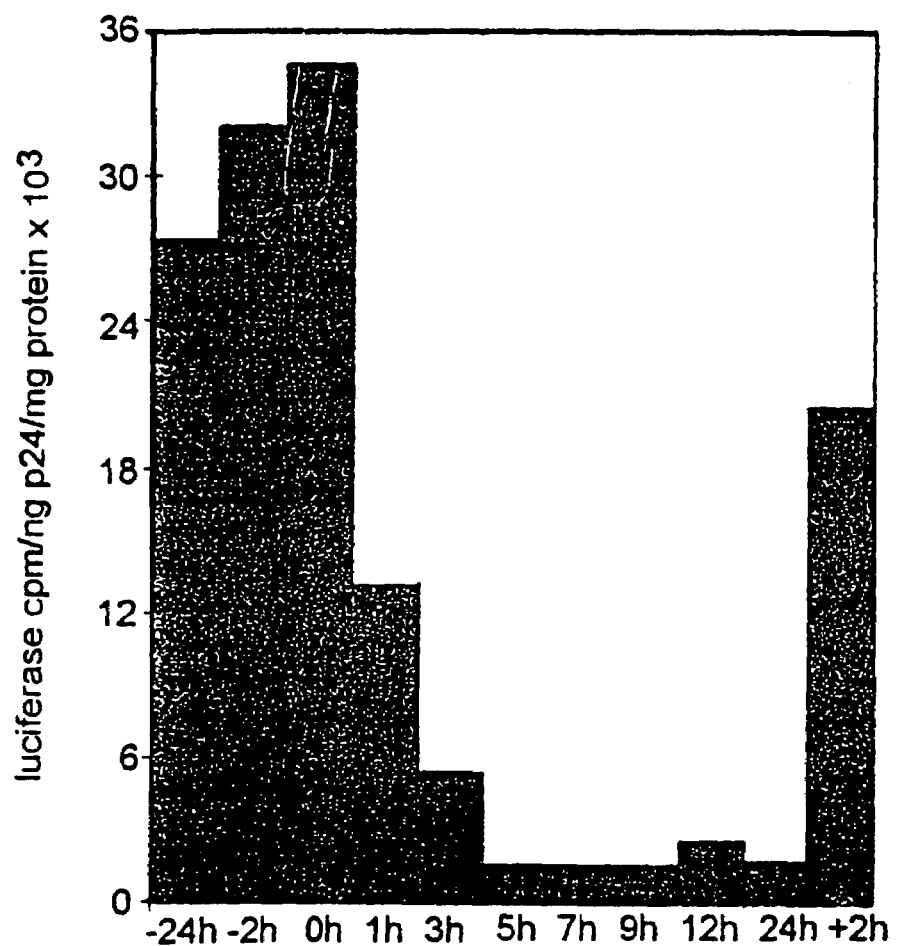
Figure 3B:
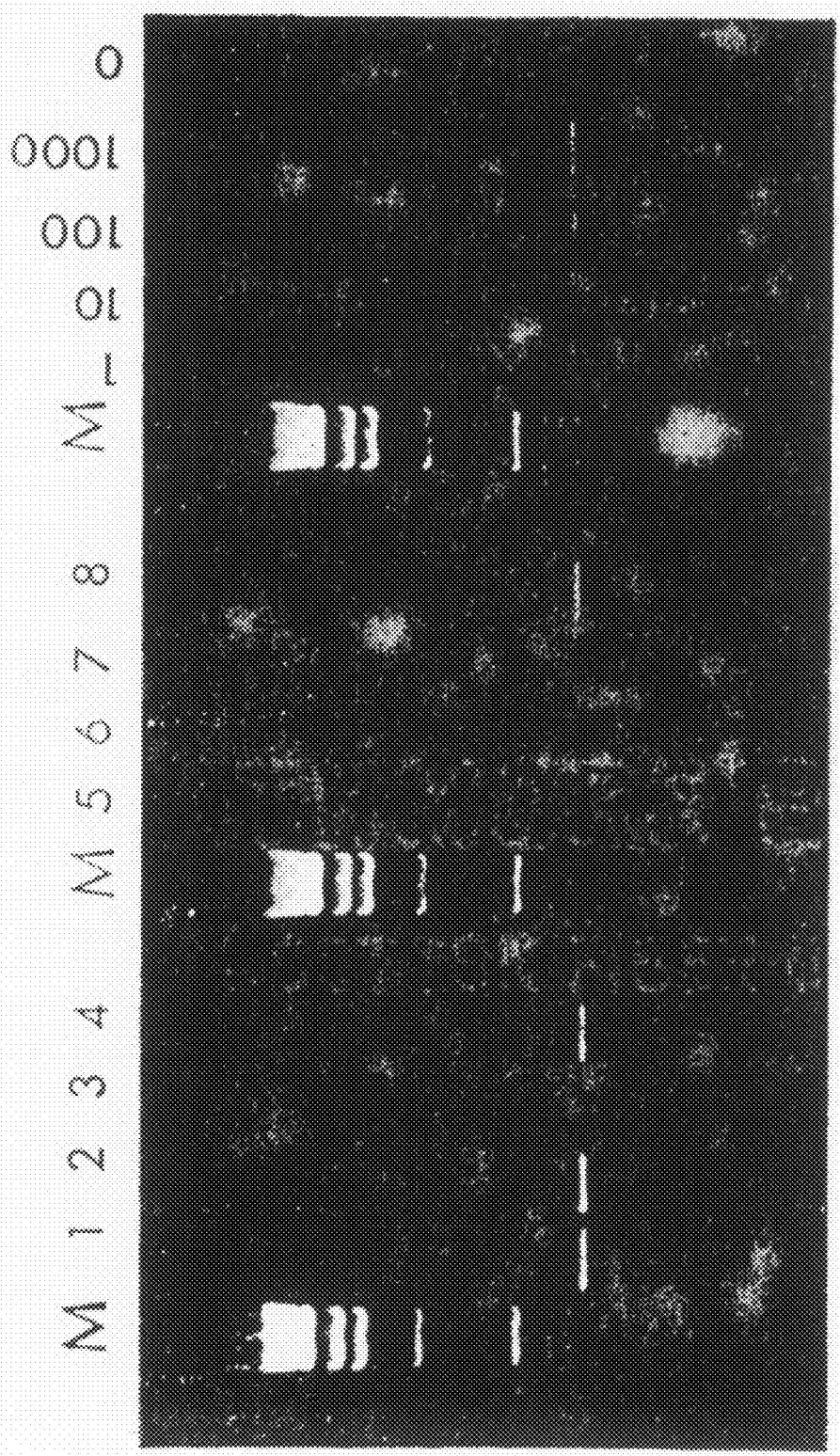

It was determined when β-chemokines inhibited HIV-1 replication by showing that complete inhibition of infection of PM1 cells required the continuous presence of β-chemokines for up to 5 h after addition of ADA or BaL env-complemented virus (FIG. 3a). Pre-treatment of the cells with 9-chemokines for 2 h or 24 h prior to infection had no inhibitory effect if the cells were subsequently washed before virus addition. Furthermore, adding β-chemokines 2 h after virus only minimally affected virus entry (FIG. 3a). A PCR-based assay was next used to detect HIV-1 early DNA reverse transcripts in PM1 cells after 10 h of infection; reverse transcription of ADA, but not of NL4/3, could not be detected in the presence of MIP-1β and RANTES (FIG. 3b). Thus, inhibition by β-chemokines requires their presence during at least one of the early stages of HIV-1 replication: virus attachment, fusion and early reverse transcription.

As described in part in the First Series of Experiments, these sites of action were discriminated, first by testing whether β-chemokines inhibited binding of JR-FL or BRU (LAI) gp120 to soluble CD4, or of tetrameric CD4-IgG2 binding to HeLa-JR-FL cells expressing oligomeric envelope glycoproteins (17). No inhibition by any of the β-chemokines was found in either assay, whereas the OKT4a CD4-MAb was strongly inhibitory in both (FIG. 2 and data not shown). Thus, β-chemokines inhibit a step after CD4 binding, when conformational changes in the envelope glycoproteins lead to fusion of the viral and cellular membranes (18). Cell-cell membrane fusion is also induced by the gp120-CD4 interaction, and can be monitored directly by resonance energy transfer (RET) between fluorescent dyes incorporated into cell membranes (17). In the RET assay, OKT4a completely inhibits membrane fusion of PM1 cells with HeLa cells expressing the envelope glycoproteins of either JR-FL (HeLa-JR-FL, the same cell line referred to above as HeLa-env$_{JR-FL}$) or BRU (HeLa-BRU, the same cell line referred to above as HeLa-env$_{LAI}$), confirming the specificity of the process (17). RANTES, MIP-1β (and to a lesser extent, MIP-1α) strongly inhibited membrane fusion of HeLa-JR-FL cells with PM1 cells, whereas fusion between PM1 cells and HeLa-BRU cells was insensitive to these β-chemokines (FIG. 1 and Table 2a).

TABLE 2

Effect of β-chemokines on HIV-1 envelope glycoprotein-mediated
membrane fusion measured using the RET assay

| | % Fusion | |
|---|---|---|
| | HeLa-JR-FL | HeLa-BRU |
| a) PM1 cells | | |
| no chemokines | 100 | 100 |
| +R/Mα/Mβ (80/400/100) | 1 | 95 |
| +RANTES (80) | 8 | 100 |
| +MIP-1α (400) | 39 | 100 |
| +MIP-1β (100) | 13 | 93 |
| +MCP-1 (100) | 99 | 98 |
| +MCP-2 (100) | 72 | 93 |
| +MCP-3 (100) | 98 | 99 |
| b) LW5 CD4+ cells | | |
| no chemokines | 100 | 100 |
| +R/Mα/Mβ(106/533/133) | 39 | 100 |
| +RANTES (106) | 65 | 95 |
| +MIP-1α (533) | 72 | 100 |
| +MIP-1β (133) | 44 | 92 |
| +OKT4A (3 ug/ml) | 0 | 0 |

Table 2 Legend:

CD4+ target cells (mitogen-activated CD4+ lymphocytes or PM1 cells) were labeled with octadecyl rhodamine (Molecular Probes, Eugene, Oreg.), and HeLa-JR-FL cells, HeLa-BRU cells (or control HeLa cells, not shown) were labeled with octadecyl fluorescein (Molecular Probes), overnight at 37° C. Equal numbers of labeled target cells and env-expressing cells were mixed in 96-well plates and β-chemokines (or CD4 MAb OKT4a) were added at the final concentrations (ng/ml) indicated in parentheses in the first column. Fluorescence emission values were determined 4 h after cell mixing (17). If cell fusion occurs, the dyes are closely associated in the conjoined membrane such that excitation of fluorescein at 450 nm results in resonance energy transfer (RET) and emission by rhodamine at 590 nm. Percentage fusion is defined as equal to 100×[(Exp RET−Min RET)/(Max RET−Min RET)], where Max RET=% RET obtained when HeLa-Env and CD4+ cells are mixed, Exp RET=% RET obtained when HeLa-Env and CD4+ cells are mixed in the presence of fusion-inhibitory compounds, and Min RET=% RET obtained when HeLa cells (lacking HIV-1 envelope glycoproteins) and CD4+ cells are mixed. The % RET value is defined by a calculation described elsewhere (17), and each is the mean of triplicate determinations. These values were, for HeLa-JR-FL and HeLa-BRU cells respectively: PM1 cells 11.5%, 10.5%; LW5 CD4+ cells, 6.0%, 10.5%; R/Mα/Mβ, RANTES+MIP-1α+MIP-1β.

Similar results were obtained with primary CD4+ T-cells from LW5 (Table 2b), although higher concentrations of β-chemokines were required to inhibit membrane fusion in the primary cells than in PM1 cells. Thus, the actions of the β-chemokines are not restricted to the PM1 cell line. The RET assay demonstrates that β-chemokines interfere with env-mediated membrane fusion.

The simplest explanation of these results is that the binding of certain β-chemokines to their receptor(s) prevents, directly or otherwise, the fusion of HIV-1 with CD4+ T-cells. It has been known for a decade that HIV-1 requires a second receptor for entry into CD4+ cells (19-21). This function is supplied, for TCLA strains, by fusin (9). Several receptors for MIP-1α, MIP-1β and RANTES have been identified (6, 7), and β-chemokines exhibit considerable cross-reactivity in receptor usage (4-8). However, C-C CKR-1 and, especially, C-C CKR-5 were identified as the most likely candidates, based on tissue expression patterns and their abilities to bind MIP-1α, MIP-1β and RANTES (4, 7, 8, 15, 22). C-C CKR-1, C-C CKR-5 and LESTR are each expressed at the mRNA level in PM1 cells and primary macrophages (data not shown). These and other β-chemokine receptors were therefore PCR-amplified, cloned and expressed.

The expression of C-C CKR-5 in HeLa-CD4 (human), COS-CD4 (simian) and 3T3-CD4 (murine) cells rendered each of them readily infectible by the primary, NSI strains ADA and BaL in the env-complementation assay of HIV-1 entry (Table 3)

TABLE 3

C-C CKR-5 expression permits infection of CD4-expressing cells by primary, NSI HIV-1 strains

| | | pcDNA3.1 | LESTR | CKR-1 | CKR-2a | CKR-3 | CKR-4 | CKR-5 | R/Mα/Mβ CKR-5 |
|---|---|---|---|---|---|---|---|---|---|
| COS-CD4 | ADA | 798 | 456 | 600 | 816 | 516 | 534 | 153000 | 3210 |
| | BaL | 660 | 378 | 600 | 636 | 516 | 618 | 58800 | 756 |
| | HxB2 | 5800 | 96700 | 5240 | 5070 | 5470 | 5620 | 4850 | 5000 |
| HeLa-CD4 | ADA | 678 | 558 | 4500 | 912 | 558 | 600 | 310000 | 6336 |
| | BaL | 630 | 738 | 1800 | 654 | 516 | 636 | 104000 | 750 |
| | HxB2 | 337000 | nd | nd | nd | nd | nd | nd | 356000 |
| 3T3-CD4 | ADA | 468 | 558 | 450 | 618 | 534 | 606 | 28400 | 1220 |
| | BaL | 606 | 738 | 660 | 738 | 534 | 558 | 11700 | 756 |
| | HxB2 | 456 | 24800 | 618 | 672 | 732 | 606 | 618 | 606 |

Table 3 Legend:

Chemokine receptor genes C-C CKR-1, C-C CKR-2a, C-C CKR-3, C-C CKR-4 and C-C CKR-5 have no introns (4-8, 15, 22) and were isolated by PCR performed directly on a human genomic DNA pool derived from the PBMC of seven healthy donors. Oligonucleotides overlapping the ATG and the stop codons and containing BamHI and XhoI restriction sites for directional cloning into the pcDNA3.1 expression vector (Invitrogen Inc.) were used. LESTR (also known as fusin or HUMSTR) (4, 9, 24) was cloned by PCR performed directly on cDNA derived from PM1 cells, using sequences derived from the NIH database. Listed below are the 5' and 3' primer pairs used in first (5-1 and 3-1) and second (5-2 and 3-2) round PCR amplification of the CKR genes directly from human genomic DNA, and of LESTR from PM1 cDNA. Only a single set of primers was used to amplify CKR-5.

```
LESTR:
L/5-1 = AAG CTT GGA GAA CCA GCG GTT ACC ATG GAG GGG ATC (SEQ ID NO: 6);

L/5-2 = GTC TGA GTC TGA GTC AAG CTT GGA GAA CCA (SEQ ID NO: 7);

L/3-1 = CTC GAG CAT CTG TGT TAG CTG GAG TGA AAA CTT GAA GAC TC (SEQ ID NO: 8);

L/3-2 = GTC TGA GTC TGA GTC CTC GAG CAT CTG TGT (SEQ ID NO: 9);

CKR-1:
C1/5-1 = AAG CTT CAG AGA GAA GCC GGG ATG GAA ACT CC (SEQ ID NO: 10);

C1/5-2 = GTC TGA GTC TGA GTC AAG CTT CAG AGA GAA (SEQ ID NO: 11);

C1/3-1 = CTC GAG CTG AGT CAG AAC CCA GCA GAG AGT TC (SEQ ID NO: 12);

C1/3-2 = GTC TGA GTC TGA GTC CTC GAG CTG AGT CAG (SEQ ID NO: 13);

CKR-2a:
C2/5-1 = AAG CTT CAG TAC ATC CAC AAC ATG CTG TCC AC (SEQ ID NO: 14);

C2/5-2 = GTC TGA GTC TGA GTC AAG CTT CAG TAC ATC (SEQ ID NO: 15);

C2/3-1 = CTC GAG CCT CGT TTT ATA AAC CAG CCG AGA C (SEQ ID NO: 16);

C2/3-2 = GTC TGA GTC TGA GTC CTC GAG CCT CGT TTT (SEQ ID NO: 17);

CKR-3:
C3/5-1 = AAG CTT CAG GGA GAA GTG AAA TGA CAA CC (SEQ ID NO: 18);

C3/5-2 = GTC TGA GTC TGA GTC AAG CTT CAG GGA GAA (SEQ ID NO: 19);

C3/3-1 = CTC GAG CAG ACC TAA AAC ACA ATA GAG AGT TCC (SEQ ID NO: 20);

C3/3-2 = GTC TGA GTC TGA GTC CTC GAG CAG ACC TAA (SEQ ID NO: 21);

CKR-4:
C4/5-1 = AAG CTT CTG TAG AGT TAA AAA ATG AAC CCC ACG G (SEQ ID NO: 22);

C4/5-2 = GTC TGA GTC TGA GTC AAG CTT CTG TAG AGT (SEQ ID NO: 23);

C4/3-1 = CTC GAG CCA TTT CAT TTT TCT ACA GGA CAG CAT C (SEQ ID NO: 24);

C4/3-2 = GTC TGA GTC TGA GTC CTC GAG CCA TTT CAT (SEQ ID NO: 25);

CKR-5:
C5/5-12 = GTC TGA GTC TGA GTC AAG CTT AAC AAG ATG GAT TAT CAA (SEQ ID NO: 26);

C5/3-12 = GTC TGA GTC TGA GTC CTC GAG TCC GTG TCA CAA GCC CAC (SEQ ID NO: 37).
```

The human CD4-expressing cell lines HeLa-CD4 (P42), 3T3-CD4 (sc6) and COS-CD4 (Z28T1) (23) were transfected with the different pcDNA3.1-CKR constructs by the calcium phosphate method, then infected 48 h later with different reporter viruses (200 ng of HIV-1 p24/$10^6$ cells) in the presence or absence of β-chemokines (400 ng/ml each of RANTES, MIP-1α and MIP-1β). Luciferase activity in cell lysates was measured 48 h later (10, 11). β-Chemokine blocking data is only shown for C-C CKR-5, as infection mediated by the other C-C CKR genes was too weak for inhibition to be quantifiable. In PCR-based assays of HIV-1 entry, a low level of entry of NL4/3 and ADA into C-C CKR-1 expressing cells (data not shown) was consistently observed.

Neither LESTR nor C-C CKR-1, -2a, -3 or -4 could substitute for C-C CKR-5 in this assay. The expression of LESTR in COS-CD4 and 3T3-CD4 cells permitted HxB2 entry, and HxB2 readily entered untransfected (or control plasmid-transfected) HeLa-CD4 cells (Table 3). Entry of BAL and ADA into all three C-C CKR-5-expressing cell lines was almost completely inhibited by the combination of MIP-1α, MIP-1β and RANTES, whereas HxB2 entry into LESTR-expressing cells was insensitive to β chemokines (Table 3). These results suggest that C-C CKR-5 functions as a β-chemokine-sensitive second receptor for primary, NSI HIV-1 strains.

The second receptor function of C-C CKR-5 was confirmed in assays of env-mediated membrane fusion. When C-C CKR-5 was transiently expressed in COS and HeLa cell lines that permanently expressed human CD4, both cell lines fused strongly with HeLa cells expressing the JR-FL envelope glycoproteins, whereas no fusion occurred when control plasmids were used (data not shown). Expression of LESTR instead of C-C CKR-5 did not permit either COS-CD4 or HeLa-CD4 cells to fuse with HeLa-JR-FL cells, but did allow fusion between COS-CD4 cells and HeLa-BRU cells (data not shown).

The fusion capacity of β-chemokine receptors was also tested in the RET assay. The expression of C-C CKR-5, but not of C-C CKR-1, -2a, -3 or -4, permitted strong fusion between HeLa-CD4 cells and HeLa-JR-FL cells. The extent of fusion between HeLa-JR-FL cells and C-C CKR-5-expressing HeLa-CD4 cells was greater than the constitutive level of fusion between HeLa-BRU cells and HeLa-CD4 cells (FIG. 4). The fusion-conferring function of C-C CKR-5 for primary, NSI HIV-1 strains has therefore been confirmed in two independent fusion assays.

Experimental Discussion

Together, the above results establish that MIP-1α, MIP-1β and RANTES inhibit HIV-1 infection at the entry stage, by interfering with the virus-cell fusion reaction subsequent to CD4 binding. It was also shown that C-C CKR-5 can serve as a second receptor for entry of primary NSI strains of HIV-1 into CD4+ T-cells, and that the interaction of β-chemokines with C-C CKR-5 inhibits the HIV-1 fusion reaction.

REFERENCES OF THE SECOND SERIES OF EXPERIMENTS

1. Levy, J. A., Mackewicz, C. E. & Barker, E. Immunol. Today 17, 217-224 (1996).
2. Cocchi, F. et al. Science 270, 1811-1815 (1995).
3. Paxton, W. A. et al. Nat. Med. 2, 412-417 (1996).
4. Neote, K., DiGregorio, D., Mak, J. Y., Horuk, R., & Schall, T. J. Cell 72, 415-425 (1993).
5. Gao, J.-L. et al. J. Exp. Med. 177, 1421-1427 (1993).
6. Bacon, K. B., Premack, B. A., Gardner, P. & Schall, T. J. Science 269, 1727-1729 (1995).
7. Raport, C. J. et al. J. Leukoc. Biol. 59, 18-23 (1996).
8. Wells, T. N. C. et al. J. Leukoc. Biol. 59, 53-60 (1996).
9. Feng, Y., Broder, C. C., Kennedy, P. E. & Berger, E. A. Science 272, 872-877 (1996).
10. Chen, B. K., Saksela, K., Andino, R. & Baltimore, D. J. Virol. 68, 654-660 (1994).
11. Connor, R. I., Chen, B. K., Choe, S., & Landau, N. R. Virology 206, 935-944 (1995).
12. Lusso, P. et al. J. Virol. 69, 3712-3720 (1995).
13. Charo, I. F. et al. Proc. Natl. Acad. Sci. USA 91, 2752-2756 (1994).
14. Ben-Baruch, A. et al. J. Biol. Chem. 270, 22123-22128 (1995).
15. Combadiere, C et al. J. Biol. Chem. 270, 29671-29675 (1995).
16. Lip, J. P., D'Andrea, A. D., Lodish, H. F. & Baltimore, D. Nature 343, 762-764 (1990).
17. Litwin, V. et al. J. Virol. (submitted for publication).
18. Moore, J. P., Jameson, B. A., Weiss, R. A. & Sattentau, Q. J. in Viral Fusion Mechanisms (ed Bentz, J.) 233-289 (CRC Press Inc, Boca Raton, USA, 1993).
19. Maddon, P. J. et al. Cell 47, 333-348 (1986).
20. Ashorn, P. A., Berger, E. A. & Moss, B. J. Virol. 64, 2149-2156 (1990).
21. Clapham, P. R., Blanc, D. & Weiss, R. A. Virology 181, 703-715 (1991).
22. Samson, M., Labbe, O., Mollereau, C., Vassart, G. & Parmentier, M. Biochemistry 11, 3362-3367 (1996).
23. Dragic, T., Charneau, P., Clavel, F. & Alizon, M. J. Virol. 66, 4794-4802 (1992)
24. Loetscher, M. et al. J. Biol. Chem. 269, 232-237 (1994).
25. Moore, J. P. & Ho, D. D. AIDS 9 (suppl A), S117-S136 (1995).
26. Trkola, A. & Moore, J. P. (unpublished data).
27. Chaudhuri, A., et al. 1994. J. Biol. Chem. 269, 7835-7838 (1994).
28. Neote, K., Mak, J. Y., Kolakowski Jr., L. F. & Schall, T. J. Blood 84, 44-52 (1994).
29. Dragic, T., Picard, L. & Alizon, M. J. Virol. 69, 1013-1018 (1995).
30. Puri, A., Morris, S. J., Jones, P., Ryan, M. & Blumenthal, R. Virology 219, 262-267 (1996) 31

Third Series of Experiments

The chemokine SDF-1 (stromal cell-derived factor 1) is the natural ligand for Fusin/CXCR4 and blocks infection by laboratory-adapted strains of HIV-1 (Ref. 1 and 2). SDF-1 exists as at least two forms, SDF-1α and SDF-1β based on variable splicing of the SDF-1 gene (Ref. 1 and 3) In the RET assay, this chemokine specifically inhibits membrane fusion mediated by gp120/gp41 form the laboratory-adapted strain HIV$_{LAI}$ but not by gp120/gp41 from the macrophage-tropic isolate HIV-1$_{JR-FL}$ as shown in FIG. 5.

REFERENCES OF THE THIRD SERIES OF EXPERIMENTS

1. Bleul, C. C., et al. (1996) Nature 382:829-833
2. Oberlin, E., et al. (1996) Nature 382:833-835
3. Shirozu, M., et al. (1995) Genomics 28:495-500

Fourth Series of Experiments

Direct Binding of HIV-1$_{JR-FL}$ gp120 to CCR5$^+$ CD4$^-$ Cells

The direct binding of HIV-1$_{JR-FL}$ gp120 to CCR5$^+$ CD4$^-$ cells has been demonstrated. In this case, preincubation of the gp120 with sCD4 or another CD4-based molecule is required, presumably because this results in a conformational change in gp120 that exposes a chemokine receptor binding site. FIG. 6 illustrates the use of flow cytometry to measure the direct binding of sCD4/gp120 complexes to human CCR5-bearing murine L1.2 cells. Background levels of binding were observed with either biotinylated protein alone, or if gp120 from the laboratory-adapted strain HIV-1$_{LAI}$ is used in place of the HIV-1$_{JR-FL}$ gp120 (data not shown).

This assay has been adapted for drug screening purposes to a 96-well microplate format where binding of the sCD4/gp120 complexes to CCR5$^+$/CD4$^-$ cells is measured using a fluorometric plate reader. One method is as follows:

1) Plate out L1.2-CCR5$^+$ cells (approx. 500,000/well)
2) Add inhibitor for 1 hour at room temperature.
3) Wash and add biotinylated sCD4(2.5 µg/ml) and biotinylated HIV-1$_{JR-FL}$ gp120 (5 µg/ml), then incubate for 2 hours at room temperature.
4) Wash and incubate with streptavidin-phycoerythrin (100 ng/nl).
5) Wash and measure the amount of bound gp120/sCD4 using a fluorometric plate reader exciting at 530 nm and reading emission at 590 nm.

Using this method, inhibition of binding of gp120/sCD4 to CCR5 by CC-chemokines (FIG. 7) and antibodies to CCR5 that block HIV-1 infection (not shown) have been demonstrated.

Inhibition of HIV-1 Envelope-Mediated Membrane Fusion by the Bicyclam, JM3100.

The bicyclam JM3100, obtained from Dr. J. Moore (Aaron Diamond AIDS Research Center, NY) was tested for ability to inhibit membrane fusion mediated by the envelope glycoproteins of the LAI or JR-FL strains of HIV-1 using the resonance energy transfer (RET) assay described above. As illustrated in FIG. 7, this molecule specifically and potently inhibits fusion mediated by gp120/gp41 from the HIV-1$_{LAI}$ strain, and not from the HIV-1$_{JR-FL}$ strain. These data suggest that this molecule specifically inhibits HIV fusion by blocking the interaction between HIV-1$_{LAI}$ gp120 and CXCR4.

Fifth Series of Experiments

CCR5 Receptor Binding Assay

Materials:
1. CCR5$^+$/L1.2 cell line
2. L1.2 cell line
3. JRFL-gp120, biotinylated
4. sCD4, unconjugated (Intracell, Cat #13101)
5. 96-well round bottom plate (Corning, cat #25850)
6. Streptavidin, phycoerythrin conjugated [SA-PE] (Becton Dickinson, cat #349023)
7. PBS without Calcium and Magnesium [PBS(−)] (Gibco BRL, cat #14190)

Method:
1. Culture CCR5+ and parental L1.2 cells and treat with sodium butyrate as described (Wu et al., J. Exp. Med 185: 1681).
2. Add cells to 96-well plate (~3×10$^5$ cells/well)
3. Centrifuge plate and remove supernatant.
4. Dilute inhibitory compounds as desired in PBS(−)/0.1% NaN$_3$. Add 40 µl of inhibitory compounds to cells. Add 40 µl of PBS(−)/0.16 NaN$_3$ to wells without inhibitory compounds.
5. Shake plate to suspend cells in solution. Incubate at room temperature for 1 hour.
6. Prepare an equimolar (~50 nM) mixture of sCD4 and biotinylated gp120. Add 40 µl of sCD4:biotinylated gp120 complex per well. (Final volume in well=80 µl). Shake plate to suspend cells in protein solution. Incubate at room temperature for one hour.
7. Centrifuge plate and remove supernatant. Add 200 µl of PBS(−) 0.1% NaN$_3$ per well. Repeat this washing procedure, for a total of three washes.
8. Centrifuge plate and remove supernatant. Dilute SA-PE 1:50 in PBS(−)/0.1-% NaN$_3$ and add 40 µl of diluted reagent to cells. Shake plate to suspend cells in solution. Incubate at room temperature for one hour.
9. Centrifuge plate as above and remove supernatant. Add 200 µl of PBS(−)/0.1% NaN$_3$ per well. Repeat this washing procedure for a total of three washes.
10. Centrifuge plate as above and remove supernatant. Add 200 µl of PBS(−)/0.1% NaN$_3$ per well.
11. Centrifuge plate and measure the fluorescence. Emission at 590 nm following excitation at 530 nm.
12. % Inhibition is calculated by using the following formula:

$$\% \text{ Inhibition} = [\text{Max} - \text{Reading}]/[\text{Max} - \text{Min}]$$

Max=Average of values in wells containing [sCD4: biotinylated gp120 w/CCR5+/L1.2 cells, no inhibitor]
Min=Average of values in wells containing sCD4:biotinylated gp120 w/L1.2 cells, no inhibitor.
Reading=Value in specific well

---

What is claimed is:

1. A monoclonal antibody which (a) binds to a CCR5 chemokine receptor on the surface of a CCR5+ CD4+ human cell; (b) inhibits fusion of HIV-1$_{JR-FL}$ with a PM-1 cell; (c) does not inhibit fusion of HIV-1$_{BRU}$ with a PM-1 cell; (d) does not activate an inflammatory response upon binding to the CCR5 chemokine receptor on the surface of the CCR5+ CD4+ cell; (e) competes with RANTES, MIP-1α and MIP-1β for binding to the CCR5 chemokine receptor on the surface of the CCR5+, CD4+ cell; and (f) inhibits binding of HIV-1$_{JR-FL}$ gp120 to the CCR5+, CD4+ cell.

* * * * *

```
                        SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
        (A) LENGTH: 38 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 1:

CAAGGCTACT TCCCTGATTG GCAGAACTAC ACACCAGG                                 38

(2) INFORMATION FOR SEQ ID NO: 2:

(i) SEQUENCE CHARACTERISTICS:
        (A) LENGTH: 25 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 2:

AGCAAGCCGA GTCCTGCGTC GAGAG                                              25

(2) INFORMATION FOR SEQ ID NO: 3:

(i) SEQUENCE CHARACTERISTICS:
        (A) LENGTH: 23 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 3:

GGGACTTTCC GCTGGGGACT TTC                                                23

(2) INFORMATION FOR SEQ ID NO: 4:
```

```
          (i) SEQUENCE CHARACTERISTICS:
              (A) LENGTH: 33 nucleotides
              (B) TYPE: nucleic acid
              (C) STRANDEDNESS: single
              (D) TOPOLOGY: linear (ii) MOLECULE TYPE: oligonucleotide (xi) SEQUENCE DESCRIPTION: SEQ ID NO: 4:

CCTGTTCGGG CGCCACTGCT AGAGATTTTC CAC                                           33

(2) INFORMATION FOR SEQ ID NO: 5:

(i) SEQUENCE CHARACTERISTICS:
              (A) LENGTH: 60 amino acids
              (B) TYPE: amino acid
              (C) STRANDEDNESS: n/a
              (D) TOPOLOGY: n/a (ii) MOLECULE TYPE: protein (xi) SEQUENCE DESCRIPTION: SEQ ID NO: 5:

Pro Cys Cys Phe Ala Tyr Ile Ala Arg Pro Leu Pro Arg Ala His Ile Lys
1               5                   10                  15

Glu Tyr Phe Tyr Thr Ser Gly Lys Cys Ser Asn Pro Ala Val Val Phe Val
        20                  25                  30

Thr Arg Lys Asn Arg Gln Val Cys Ala Asn Pro Glu Lys Lys Trp Val Arg
 35              40                  45                  50

Glu Tyr Ile Asn Ser Leu Glu Met Ser
                55                  60

(2) INFORMATION FOR SEQ ID NO: 6:

(i) SEQUENCE CHARACTERISTICS:
              (A) LENGTH: 36 nucleotides
              (B) TYPE: nucleic acid
              (C) STRANDEDNESS: single
              (D) TOPOLOGY: linear (ii) MOLECULE TYPE: oligonucleotide (xi) SEQUENCE DESCRIPTION: SEQ ID NO: 6:

AAGCTTGGAG AACCAGCGGT TACCATGGAG GGGATC                                        36

(2) INFORMATION FOR SEQ ID NO: 7:

(i) SEQUENCE CHARACTERISTICS:
              (A) LENGTH: 30 nucleotides
              (B) TYPE: nucleic acid
              (C) STRANDEDNESS: single
              (D) TOPOLOGY: linear (ii) MOLECULE TYPE: oligonucleotide (xi) SEQUENCE DESCRIPTION: SEQ ID NO: 7:

GTCTGAGTCT GAGTCAAGCT TGGAGAACCA                                               30

(2) INFORMATION FOR SEQ ID NO: 8:

(i) SEQUENCE CHARACTERISTICS:
              (A) LENGTH: 41 nucleotides
              (B) TYPE: nucleic acid
              (C) STRANDEDNESS: single
              (D) TOPOLOGY: linear (ii) MOLECULE TYPE: oligonucleotide (xi) SEQUENCE DESCRIPTION: SEQ ID NO: 8:
```

CTCGAGCATC TGTGTTAGCT GGAGTGAAAA CTTGAAGACT C                41

(2) INFORMATION FOR SEQ ID NO: 9:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 9:

GTCTGAGTCT GAGTCCTCGA GCATCTGTGT                             30

(2) INFORMATION FOR SEQ ID NO: 10:

(i) SEQUENCE CHARACTERISTICS:
        (A) LENGTH: 32 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 10:

AAGCTTCAGA GAGAAGCCGG GATGGAAACT CC                          32

(2) INFORMATION FOR SEQ ID NO: 11:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 11:

GTCTGAGTCT GAGTCAAGCT TCAGAGAGAA                             30

(2) INFORMATION FOR SEQ ID NO: 12:

(i) SEQUENCE CHARACTERISTICS:
        (A) LENGTH: 32 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 12:

CTCGAGCTGA GTCAGAACCC AGCAGAGAGT TC                          32

(2) INFORMATION FOR SEQ ID NO: 13:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 13:

GTCTGAGTCT GAGTCCTCGA GCTGAGTCAG                             30

(2) INFORMATION FOR SEQ ID NO: 14:

(i) SEQUENCE CHARACTERISTICS:
            (A) LENGTH: 32 nucleotides
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO: 14:

AAGCTTCAGT ACATCCACAA CATGCTGTCC AC                              32

(2) INFORMATION FOR SEQ ID NO: 15:

(i) SEQUENCE CHARACTERISTICS:
            (A) LENGTH: 30 nucleotides
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO: 15:

GTCTGAGTCT GAGTCAAGCT TCAGTACATC                                 30

(2) INFORMATION FOR SEQ ID NO: 16:

(i) SEQUENCE CHARACTERISTICS:
            (A) LENGTH: 31 nucleotides
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO: 16:

CTCGAGCCTC GTTTTATAAA CCAGCCGAGA C                               31

(2) INFORMATION FOR SEQ ID NO: 17:

(i) SEQUENCE CHARACTERISTICS:
            (A) LENGTH: 30 nucleotides
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO: 17:

GTCTGAGTCT GAGTCCTCGA GCCTCGTTTT                                 30

(2) INFORMATION FOR SEQ ID NO: 18:

(i) SEQUENCE CHARACTERISTICS:
            (A) LENGTH: 29 nucleotides
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO: 18:

AAGCTTCAGG GAGAAGTGAA ATGACAACC                                  29

(2) INFORMATION FOR SEQ ID NO: 19:

(i) SEQUENCE CHARACTERISTICS:
            (A) LENGTH: 30 nucleotides
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO: 19:

GTCTGAGTCT GAGTCAAGCT TCAGGGAGAA                                    30

(2) INFORMATION FOR SEQ ID NO: 20:

(i) SEQUENCE CHARACTERISTICS:
          (A) LENGTH: 33 nucleotides
          (B) TYPE: nucleic acid
          (C) STRANDEDNESS: single
          (D) TOPOLOGY: linear (ii) MOLECULE TYPE: oligonucleotide (xi) SEQUENCE DESCRIPTION: SEQ ID NO: 20:

CTCGAGCAGA CCTAAAACAC AATAGAGAGT TCC                                33

(2) INFORMATION FOR SEQ ID NO: 21:

(i) SEQUENCE CHARACTERISTICS:
          (A) LENGTH: 30 nucleotides
          (B) TYPE: nucleic acid
          (C) STRANDEDNESS: single
          (D) TOPOLOGY: linear (ii) MOLECULE TYPE: oligonucleotide (xi) SEQUENCE DESCRIPTION: SEQ ID NO: 21:

GTCTGAGTCT GAGTCCTCGA GCAGACCTAA                                    30

(2) INFORMATION FOR SEQ ID NO: 22:

(i) SEQUENCE CHARACTERISTICS:
          (A) LENGTH: 34 nucleotides
          (B) TYPE: nucleic acid
          (C) STRANDEDNESS: single
          (D) TOPOLOGY: linear (ii) MOLECULE TYPE: oligonucleotide (xi) SEQUENCE DESCRIPTION: SEQ ID NO: 22:

AAGCTTCTGT AGAGTTAAAA AATGAACCCC ACGG                               34

(2) INFORMATION FOR SEQ ID NO: 23:

(i) SEQUENCE CHARACTERISTICS:
          (A) LENGTH: 30 nucleotides
          (B) TYPE: nucleic acid
          (C) STRANDEDNESS: single
          (D) TOPOLOGY: linear (ii) MOLECULE TYPE: oligonucleotide (xi) SEQUENCE DESCRIPTION: SEQ ID NO: 23:

GTCTGAGTCT GAGTCAAGCT TCTGTAGAGT                                    30

(2) INFORMATION FOR SEQ ID NO: 24:

(i) SEQUENCE CHARACTERISTICS:
          (A) LENGTH: 34 nucleotides
          (B) TYPE: nucleic acid
          (C) STRANDEDNESS: single
          (D) TOPOLOGY: linear (ii) MOLECULE TYPE: oligonucleotide (xi) SEQUENCE DESCRIPTION: SEQ ID NO: 24:

```
CTCGAGCCAT TTCATTTTTC TACAGGACAG CATC                          34

(2) INFORMATION FOR SEQ ID NO: 25:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 25:

GTCTGAGTCT GAGTCCTCGA GCCATTTCAT                                30

(2) INFORMATION FOR SEQ ID NO: 26:

(i) SEQUENCE CHARACTERISTICS:
        (A) LENGTH: 39 nucleotides
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 26:

GTCTGAGTCT GAGTCAAGCT TAACAAGATG GATTATCAA                      39

(2) INFORMATION FOR SEQ ID NO: 27:

(i) SEQUENCE CHARACTERISTICS:
        (A) LENGTH: 39 nucleotides
        (B) TYPE: nucleic acid
        (C) STRANDEDNESS: single
        (D) TOPOLOGY: linear (ii) MOLECULE TYPE: oligonucleotides (xi) SEQUENCE DESCRIPTION: SEQ ID NO: 27:

GTCTGAGTCT GAGTCCTCGA GTCCGTGTCA CAAGCCCAC                       39
```